United States Patent
Laing et al.

(10) Patent No.: US 12,215,356 B2
(45) Date of Patent: *Feb. 4, 2025

(54) METHODS OF PREPARING A PRIMARY CELL SAMPLE

(71) Applicant: Celcuity Inc., Minneapolis, MN (US)

(72) Inventors: Lance Gavin Laing, Orono, MN (US); Ben Rich, Minneapolis, MN (US); Abhijit Dandapat, Minneapolis, MN (US)

(73) Assignee: Celcuity Inc., Minneapolis, MN (US)

( * ) Notice: Subject to any disclaimer, the term of this patent is extended or adjusted under 35 U.S.C. 154(b) by 79 days.

This patent is subject to a terminal disclaimer.

(21) Appl. No.: 18/100,437

(22) Filed: Jan. 23, 2023

(65) Prior Publication Data

US 2023/0235293 A1 Jul. 27, 2023

Related U.S. Application Data

(63) Continuation of application No. 15/950,739, filed on Apr. 11, 2018, now Pat. No. 11,591,573, which is a continuation of application No. PCT/US2016/057923, filed on Oct. 20, 2016.

(60) Provisional application No. 62/243,765, filed on Oct. 20, 2015.

(51) Int. Cl.
*C12N 5/09* (2010.01)
*C12N 5/00* (2006.01)
*C12N 5/07* (2010.01)

(52) U.S. Cl.
CPC .......... *C12N 5/0693* (2013.01); *C12N 5/0018* (2013.01); *C12N 5/06* (2013.01); *C12N 2500/02* (2013.01); *C12N 2501/48* (2013.01); *C12N 2501/727* (2013.01); *C12N 2501/734* (2013.01); *C12N 2503/00* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,712,161 | A | 1/1998 | Koezuka et al. |
| 5,858,678 | A | 1/1999 | Chinnadurai |
| 8,252,591 | B2 | 8/2012 | Ince et al. |
| 8,936,939 | B2 | 1/2015 | Ince et al. |
| 9,096,827 | B2 | 8/2015 | Meiron et al. |
| 9,114,193 | B2 | 8/2015 | Feng et al. |
| 11,591,573 | B2 * | 2/2023 | Laing .................. C12N 5/0693 |
| 2008/0299540 | A1 | 12/2008 | Ince et al. |
| 2009/0130064 | A1 | 5/2009 | Rogiers et al. |
| 2013/0012404 | A1 | 1/2013 | Inoue |
| 2013/0130376 | A1 | 5/2013 | Serobyan et al. |
| 2013/0330761 | A1 | 12/2013 | Laing et al. |
| 2014/0142000 | A1 | 5/2014 | Tung et al. |
| 2015/0125894 | A1 | 5/2015 | Laing et al. |
| 2018/0230434 | A1 | 8/2018 | Laing et al. |

FOREIGN PATENT DOCUMENTS

| | | | |
|---|---|---|---|
| EP | 1 795 897 A1 | 6/2007 | |
| WO | 2009/066258 A1 | 5/2009 | |
| WO | 2011/090068 A1 | 7/2011 | |
| WO | 2013/050962 A1 | 4/2013 | |
| WO | WO-2014117021 A2 * | 7/2014 | .............. A61P 35/00 |
| WO | 2014/132032 A1 | 9/2014 | |
| WO | WO-2015089380 A2 * | 6/2015 | ........... A61K 31/337 |
| WO | 2015/156929 A1 | 10/2015 | |

OTHER PUBLICATIONS

Si-Tayeb et al. Matrix Metalloproteinase 3 Is Present in the Cell Nucleus and Is Involved in Apoptosis, The American Journal of Pathology, vol. 169, No. 4, Oct. 2006 (Year: 2006).*
12634—Advanced D-MEM/F-12, Thermo Fischer Scientific, [Date of Retrieval: Jul. 10, 2020], Internet <URL:https://www.thermofisher.com/jp/ja/home/technical-resources/media-formulation.227.html>.
American Type Culture Collection: "Formulation for DMEM:F-12 Medium", 1 page (2013).
American Type Culture Collection: "Formulation for Dulbecco's Modified Eagle's Medium (DMEM) ATCC(R) 30-2002," 1 page (2013).
Anderson, D.G et al., "Nanoliter-scale synthesis of arrayed biomaterials and application to human embryonic stem cells," Nat. Biotechnol., vol. 22:863-866 (2004).
Atkuri, K.R., et al., "Importance of culturing primary lymphocytes at physiological oxygen levels," Proc. Nat. Acad. Sci., vol. 104(11): 4547-4552 (2007).
Brahimi-Horn, M.C., et al., "Hypoxia and cancer," J. Molec. Med., vol. 85(12), 1301-1307 (2007).
Cooper, P., et al., "Critical effect of oxygen tension on rate of growth of animal cells in continuous suspended culture," Nature, vol. 182: 1508-1509. (1958).

(Continued)

*Primary Examiner* — Kevin K Hill
*Assistant Examiner* — Alexandra F Connors
(74) *Attorney, Agent, or Firm* — Nelson Mullins Riley & Scarborough LLP; Jane E. Remillard, Esq.; Jill Gorny Sloper, Esq.

(57) ABSTRACT

The invention provides methods of preparing a sample of viable diseased cells obtained from a human subject for clinical testing, wherein the methods inhibit anoikis and/or anoikis in the cells while maintaining the physiological functions and genomic composition of the cells when they were in vivo. In the methods of the invention, primary cells are cultured in media comprising at least one anoikis inhibitor, preferably at least one inhibitor of an intrinsic anoikis pathway and at least one inhibitor of an extrinsic anoikis pathway, under anti-anoikis atmospheric conditions, such as greater than 2% and less than 20% oxygen. Method combining multiple culturing conditions, including surface attachment under conditions that inhibit anoikis, are also provided. Compositions and kits for use in the methods of the invention are also provided.

10 Claims, No Drawings

(56) References Cited

OTHER PUBLICATIONS

Crystal, A.S. et al., "Patient-derived models of acquired resistance can identify effective drug combinations for cancer," Science 346:1480-1486 (2014).
Danet, G.H., et al., "Expansion of human SCID-repopulating cells under hypoxic conditions," J. Clin. Invest., vol. 112: 126-135. (2003).
Falsey, J.R. et al. "Peptide and small molecule microarray for high throughput cell adhesion and functional assays," Bioconjug. Chem., vol. 12:346-353 (2001).
Flaim, C.J. et al., "An extracellular matrix microarray for probing cellular differentiation," Nat. Methods, vol. 2:119-125 (2005).
Frisch S.M., et al., Disruption of Epithelial Cell-Matrix Interactions Induces Apoptosis, The Journal of Cell Biology, vol. 124 (4):619-626 (1994).
Fulda, S., et al., "Extrinsic versus intrinsic apoptosis pathways in anticancer chemotherapy," Oncogene, vol. 7:4798-4811 (2006).
Hegerfeldt, Y. et al., "Collective Cell Movement in Primary Melanoma Explants: Plasticity of Cell-Cell Interaction, 1-Integrin Function, and Migration Strategies," Cancer Research, vol. 62, 2125-2130 ( 2002].
Huttenlocher, A. et al., "Adhesion in cell migration," Current Opinion in Cell Biology, vol. 7:697-706 (1995).
International Preliminary Report on Patentability, PCT/US2016/057923, dated Apr. 24, 2018, 7 pages.
International Search Report and Written Opinion, PCT/US2016/057923, dated Feb. 21, 2017, 10 pages.
Ivanovic, Z., "Hypoxia or in situ normoxia: the stem cell paradigm," J. Cell. Physiol., vol. 219(2): 271-275. (May 2009).
Kuschel, C. et al., "Cell adhesion profiling using extracellular matrix protein microarrays," Biotechniques, vol. 40:523-531 (2006).
Lengner, C.J., et al., "Derivation of pre-X inactivation human embryonic stem cells under physiological oxygen concentrations," Cell, vol. 141(5): 872-883.(2010).
P. Paoli et al. "Anoikis molecular pathways and its role in cancer progression" Biochimica et Biophysica Acta, 1833 (2013).
Packer, L., et al., "Low oxygen concentration extends the lifespan of cultured human diploid cells," Nature, vol. 267: 423-425 (1977).
Panchision, D.M., "The role of oxygen in regulating neural stem cells in development and disease," J. Cell. Physiol., vol. 220(3): 562-568 (Sep. 2009).
Parrinello, S. et al., "Oxygen sensitivity severely limits the replicative lifespan of murine fibroblasts," Nature Cell Biol., vol. 5(8):741-747 (Aug. 2003).
Richter, A., et al., "Influence of oxygen and culture media on plating efficiency of some mammalian tissue cells," J. Nat. Cancer Inst., vol. 49: 1705-1712. (1972).
Simiantonaki, N., "Hypoxia-induced epithelial VEGF-C/VEGFR-3 upregulation in carcinoma cell lines," Int. J. Oncol., vol. 32: 585-592 (2008).
Somlyo et al., "Rho-Kinase Inhibitor Retards Migration and in Vivo Dissemination of Human Prostate Cancer Cells," Biochemical and Biophysical Research Communication, vol. 269 652-659 ( 2000).
Stamenkovic Extracellular matrix remodelling: the role of matrix metalloproteinases 2003. J Pathol., vol. 200: 448-464 (2009).
StemPro hESC SFM, [online], Thermo Fischer Scientific Inc., [Date of Retrieval: Jul. 10, 2020], Internet <URL:http://tools.thermofisher.com/content/sfs/manuals/stempro_hESC_SFM_man.pdf>, 2 pages.
Wernerspach, D. et al., "Oxygen: too much of a good thing," Thermo Fisher Scientific Lab. Equip., 15 pages (2009) https://www.laboratoryequipment.com/article/2009/10/oxygen-too-much-good-thing date retrieved Jun. 1, 2018.
Wolf, K. et al., "Compensation mechanism in tumor cell migration: mesenchymal-amoeboid transition after blocking of pericellular proteolysis," The Journal of Cell Biology, vol. 160 (2):267-277 (2003).

* cited by examiner

METHODS OF PREPARING A PRIMARY CELL SAMPLE

RELATED APPLICATIONS

This application is a Continuation of U.S. Continuation application Ser. No. 15/950,739 filed on Apr. 11, 2018, which is a Continuation of Application PCT/US2016/057923 filed on Oct. 20, 2016. Application PCT/US2016/057923 claims the benefit of U.S. Provisional Application 62/243,765 filed on Oct. 20, 2015. The entire contents of the above-referenced patent applications are incorporated herein by this reference.

BACKGROUND OF THE INVENTION

A number of constraints make it difficult to obtain viable human diseased cells suitable for use as a sample in a clinical test when the cells are obtained directly from a human tissue specimen. This largely explains why there are few, if any, clinical tests that use live human cells extracted from tissue. Oftentimes, the preparation of a viable diseased cell sample must be performed at a different location than where the specimen is removed from a patient. This requires that the tissue be transported in a collection container that retains cell viability for an extended period of time. In addition, the amount of diseased tissue available for testing is limited. When the specimen is obtained during a biopsy procedure, 5-10 milligrams or less of diseased tissue may be all that is available. Conventional techniques to extract viable cells from a tissue specimen of this size yield few viable cells. A clinical test requires more than a few viable diseased cells, which would require that the extracted cells to be expanded to have a suitable number representing the tumor of the patient. This presents several additional constraints. First, the time available to expand the cells is limited. Clinical test results are ideally available within several days following the acquisition of the patient specimen to ensure timely selection of an appropriate treatment protocol. In rare cases, a clinical result may still be useful 30 days after a specimen is obtained from a patient. In most cases, the clinical test must be designed to yield a result in less than two weeks to be useful. This requires, ideally, methods to extract and expand a small number of viable cells extracted from a specimen capable of providing a sufficient number of viable diseased cells in less than two weeks.

Furthermore, for the clinical test results to be reliable, the cells must be extracted and expanded in a manner that maintains the distribution of diseased cells found originally in the specimen. This is because any clinical test involving a human specimen requires that a test sample derived from the specimen be representative of the original specimen itself. For instance, a tumor specimen is comprised of different epithelial cell types—luminal, myo, basal, stem—in a certain proportion to each other; a sample obtained from it should include these cell types in roughly similar proportions. However, when a sample of cells obtained directly from a human specimen is extracted and expanded, one cell type may proliferate at a greater rate than the others, or another cell type may not expand at all depending upon the conditions employed. Should that occur, the resulting sample would not be representative of the original specimen and thus may be compromised as a clinical sample.

A related requirement for preparation of a cell sample is that the resulting diseased cells retain their in vivo genomic and physiologic activity profile so that they retain the physiological or genomic characteristics that will be tested. For instance, to measure cell adhesion or cell signaling pathway activity, the cells' pathways ex vivo must retain their in vivo function. Otherwise, the accuracy of a clinical test result would be comprised. Another requirement is that any method used to prepare a cell sample must be capable of yielding testable cell samples from a high percentage of specimens obtained.

Current practices described in scientific literature for acquiring primary cells from tissue for research report less than a 50% success rate in obtaining viable cell samples from tumor tissue (see e.g., Crystal, A. S. et al. (2014) *Science* 346:1480-1486). The willingness of clinicians to wait up to two weeks for a clinical test result requires the likelihood of a successful test to be high enough to justify delaying treatment of their patient. Since delaying treatment for a patient entails risk, clinicians are unlikely to adopt a clinical test that imposed this risk without a reasonable likelihood that a test result of high utility will be available.

Thus, given the unique requirements of preparing a sample of viable diseased cells for clinical testing—preserving the viability of the cells during a transit period, availability of only a small amount of specimen, the short time available to expand the diseased cells, maintaining cell sample composition consistent with the original tumor, yielding a high percentage of testable cell samples, maintaining physiological and genomic characteristics—there is a need for the development of novel methods of preparing primary cell samples derived from human tissue specimens such that the sample is suitable for use in clinical testing.

SUMMARY OF THE INVENTION

The methods described herein address obstacles to preparing a sample of viable diseased cells suitable for clinical testing. The invention provides compositions and methods of preparing a sample of viable diseased cells (i.e., primary cells) obtained from a subject by culturing said viable diseased cells in a media comprising anoikis inhibitors (e.g., intrinsic and/or extrinsic anoikis inhibitors), and/or on anti-anoikis, stress reducing surfaces (e.g., hydrated extracellular matrix protein combinations), and/or in anti-anoikis, stress reducing, atmospheric conditions (e.g., greater than 2% and less than 20% oxygen) and especially during times of test sample preparation that are the most likely to cause the viable disease cells to enter into anoikis. The methods of the invention allow for preparation of sufficient numbers of primary human cells, in a sufficiently short amount of time, that maintain the physiological and genomic characteristics of the cells in vivo such that highly accurate clinical testing can be performed on them in a clinically relevant time frame.

Accordingly, in one aspect, the invention provides a method of preparing a sample of viable diseased cells obtained from a human subject for clinical testing, the method comprising:

culturing the sample of viable diseased cells obtained from the human subject in a media comprising at least one anoikis inhibitor under conditions comprising greater than 2% and less than 20% oxygen; and conducting a clinical test on the sample of viable diseased cells.

In another aspect, the invention provides a method of preparing a sample of viable diseased cells obtained from a human subject for clinical testing, the method comprising:

culturing the sample of viable diseased cells obtained from the human subject in a media comprising at least one anoikis inhibitor under conditions comprising 6-17% oxygen (e.g., 10% oxygen), e.g., for at least one hour (e.g., for 3 hours);

culturing the sample in a media comprising at least one anoikis inhibitor and lacking digestion enzymes under conditions comprising 6-17% oxygen (e.g., 10% oxygen), e.g., for at least one hour; (e.g., 3 hours); and culturing the sample in media lacking anoikis inhibitors under conditions comprising 20% oxygen, to thereby prepare the sample for clinical testing.

In another aspect, the invention provides a method of preparing a sample of viable diseased cells obtained from a human subject for clinical testing, the method comprising:

culturing the sample of viable diseased cells obtained from the human subject in a media comprising at least one anoikis inhibitor under conditions comprising 6-17% oxygen (e.g., 10% oxygen) on a cell culture vessel surface coated with a hydrated extracellular matrix (ECM).

In another aspect, the invention provides a method of preparing a sample of viable diseased cells obtained from a human subject for clinical testing, the method comprising:

culturing the sample of viable diseased cells obtained from the human subject in a media comprising at least one anoikis inhibitor under conditions comprising 6-17% oxygen (e.g., 10% oxygen) on a cell culture vessel surface coated with a hydrated extracellular matrix (ECM); and attaching the sample of viable diseased cells to a surface comprising a hydrated extracellular matrix (ECM), wherein the ECM consists of: (i) fibronectin and collagen; (ii) collagen and laminin 332 (laminin V) or (iii) laminin 332 (laminin V), to thereby prepare the sample for clinical testing.

In yet another aspect, the invention provides a method of preparing a sample of viable diseased cells obtained from a human subject for clinical testing, the method comprising:

culturing the sample of viable diseased cells obtained from the human subject in a media comprising at least one caspase inhibitor, at least one MMP3 inhibitor and at least one Rho-associated kinase inhibitor under conditions comprising 6-17% oxygen (e.g, 10% oxygen), to thereby prepare the sample for clinical testing.

In yet another aspect, the invention provides a method of preparing a sample of viable diseased cells obtained from a human subject for clinical testing using a biosensor, the method comprising:

attaching the sample of viable diseased cells to a surface comprising a hydrated extracellular matrix (ECM) consisting of fibronectin and collagen; and conducting a clinical test using a biosensor on the sample of viable diseased cells.

In yet another aspect, the invention pertains to a method of preparing a sample of viable diseased cells obtained from a human subject for clinical testing comprising: culturing the sample of viable diseased cells obtained from the human subject in a media comprising at least one anoikis inhibitor (e.g., at least one inhibitor of an intrinsic anoikis pathway and at least one inhibitor of an extrinsic anoikis pathway) under conditions comprising 6-17% oxygen (e.g., 10% oxygen);

attaching the sample of viable diseased cells to a surface comprising a hydrated extracellular matrix (ECM) consisting of fibronectin and collagen; and continuing culture of the sample attached to the surface in a media comprising at least one anoikis inhibitor under conditions comprising 6-17% oxygen (e.g., 10% oxygen).

In one embodiment, the sample is cultured in a media comprising at least one inhibitor of an intrinsic anoikis pathway and at least one inhibitor of an extrinsic anoikis pathway. In another embodiment, the sample is cultured in a media comprising at least one inhibitor of an intrinsic anoikis pathway and/or at least one inhibitor of an extrinsic anoikis pathway inhibitor, or combinations thereof. In one embodiment, the at least one apoptosis inhibitor agonizes an anti-anoikis pathway. In one embodiment, the sample is cultured in a media comprising at least one inhibitor of an anoikis pathway.

In one embodiment, the at least one anoikis inhibitor is selected from the group consisting of kinase inhibitors, protease inhibitors, stress inhibitors, death receptor inhibitors, cytochrome C inhibitors and anoikis inhibitors. In another embodiment, the at least one anoikis inhibitor is selected from the group consisting of Rho-associated kinase inhibitors, ALK5 inhibitors, caspase inhibitors, matrix metalloprotease inhibitors, redox buffering agents, reactive oxygen species inhibitors, TNFα inhibitors, TGFβ inhibitors, cytochrome C release inhibitors, carbonic anhydrase antagonists without calcium channel activation, integrin stabilizers, integrin ligands, Fas inhibitors, FasL inhibitors, Bax inhibitors and Apaf-1 inhibitors. Various non-limiting examples of anoikis inhibitors are described further herein. In certain embodiments, the media in which the cell sample is cultured comprises two or more anoikis inhibitors, such as two, three, four, five or more anoikis inhibitors. For example, in one embodiment, the sample is cultured in a media comprising at least three anoikis inhibitors, such as a Rho-associated kinase inhibitor, a caspase inhibitor and an MMP3 inhibitor used in combination. Various other non-limiting examples of combinations of anoikis inhibitors are described further herein.

In one embodiment, the sample is cultured under conditions comprising 6-17% oxygen. In another embodiment, the sample is cultured under conditions comprising 10% oxygen. In yet another embodiment, the sample is cultured under conditions comprising 17-19% oxygen. In certain embodiments, the sample is cultured under two or more different atmospheric conditions at different times, such as first culturing under conditions comprising 6-17% oxygen, such as at 10% oxygen for a period of time, and then switching the sample to different atmospheric conditions, such as comprising 1-5% oxygen, or 17-19% oxygen, or 20% oxygen. Various suitable anti-anoikis, stress-reducing atmospheric conditions are described further herein.

In certain embodiments, the sample of viable diseased cells is contacted with a digestion media for a period of time prior to culturing, wherein the digestion media digests tissue without causing anoikis, cell surface adhesion molecule damage or non-anoikis means of cell death. Typically, the digestion media comprises one or more digestion enzymes. In certain embodiments, the digestion media also comprises at least one anoikis inhibitor and may contain multiple anoikis inhibitors (e.g., at least one inhibitor of an intrinsic anoikis pathway and/or at least one inhibitor of an extrinsic apoptotic pathway). In certain embodiments, the digestion media also comprises at least one anoikis inhibitor.

The method of the invention can comprise culturing the cell sample in multiple different culture media for different periods of time and/or culturing the cell sample in culture media that comprise additional components in addition to the anoikis inhibitor(s). For example, in one embodiment, the sample of viable diseased cells is cultured in a media comprising at least one component that promotes activation of adhesion pathways. Non-limiting examples of such components are described further herein. In another embodiment, the sample of viable diseased cells is cultured in a serum free culture media comprising at least one component that preserves physiological or genomic characteristics of the viable diseased cells. Non-limiting examples of such components are described further herein. In another embodiment, the sample of viable diseased cells is cultured in a serum free media comprising at least one component that promotes cell growth, cell division or cell cycling to facilitate cell proliferation. Non-limiting examples of such components are described further herein. In another embodiment, the sample of viable diseased cells is cultured in a media comprising at least one component that promotes temporary reversal of adhesion to facilitate transfer of cells from one vessel to another vessel. Non-limiting examples of such components are described further herein.

In certain embodiments, prior to conducting the clinical test, the sample of viable diseased cells is transferred to a media lacking anoikis inhibitors. In one embodiment, the sample of viable diseased cells is cultured in the media comprising at least one anoikis inhibitor for at least 120 hours before transfer to the media lacking anoikis inhibitors. In other embodiments, the sample is cultured in the media comprising at least one anoikis inhibitor for at least 24-96 hours before transfer to the media lacking anoikis inhibitors. In one embodiment, the sample of viable diseased cells is transferred to the media lacking anoikis inhibitors under conditions comprising 20% oxygen.

In certain embodiments, prior to conducting the clinical test, the sample of viable diseased cells is attached to a surface comprising a hydrated extracellular matrix (ECM). In one embodiment, the hydrated ECM is folded. In one embodiment, the hydrated extracellular matrix (or hydrated and folded ECM) consists of fibronectin and collagen, preferably wherein the fibronectin and collagen comprise a fibrillic and hydrophilic surface. In another embodiment, the hydrated extracellular matrix (or hydrated and folded ECM) consists of a collagen-laminin 332 (laminin V) co-structure. In yet another embodiment, the hydrated extracellular matrix (or hydrated and folded ECM) consists of laminin 332 (laminin V). In one embodiment, the surface is a biosensor surface. In another embodiment, the cells surface is a cell culture vessel surface. The method can further comprise conducting a clinical test using a biosensor on the sample of viable diseased cells.

The methods of the invention are suitable for use with a wide variety of viable diseased cells obtainable from human subjects. In a preferred embodiment, the viable diseased cells are cancer cells. Furthermore, the methods of the invention are suitable for preparing primary human cells for a wide variety of in vitro clinical testing, including diagnostic tests, genetic tests, treatment regimen tests and the like. In one embodiment, the clinical test is conducted using a biosensor. In one embodiment, the clinical test comprises contacting the sample of viable diseased cells with at least one agent and measuring cell adhesion or attachment before and after contact of the sample with the at least one agent.

In another aspect, the invention pertains to a cell culture composition comprising primary human cancer cells cultured in a media comprising at least one anoikis inhibitor under conditions comprising greater than 2% and less than 20% oxygen (e.g., 6-17% oxygen, 10% oxygen). In one embodiment of the cell culture composition, the media comprises at least one inhibitor of an intrinsic anoikis pathway and at least one inhibitor of an extrinsic anoikis pathway and wherein the cells are cultured under conditions comprising 6-17% oxygen (e.g., 10% oxygen). In another embodiment of the cell culture composition, the media comprises at least three anoikis inhibitors (e.g., a Rho-associated kinase inhibitor, a caspase inhibitor and an MMP3 inhibitor) and the cells are cultured under conditions comprising 6-17% oxygen (e.g., 10% oxygen).

In another aspect, the invention pertains to a biosensor surface comprising primary human cancer cells attached to the biosensor surface via a hydrated extracellular matrix (ECM), wherein the ECM consists of: (i) fibronectin and collagen; (ii) collagen and laminin 332 (laminin V) or (iii) laminin 332 (laminin V). In one embodiment of the biosensor surface, the ECM consists of fibronectin and collagen comprising a fibrillic and hydrophilic surface. In one embodiment, the hydrated ECM is folded.

In another aspect, the invention pertains to a cell culture vessel surface comprising primary human cancer cells attached to the cell culture vessel surface via a hydrated extracellular matrix (ECM), wherein the ECM consists of: (i) fibronectin and collagen; (ii) collagen and laminin 332 (laminin V) or (iii) laminin 332 (laminin V). In one embodiment of the cell culture vessel surface, the ECM consists of fibronectin and collagen comprising a fibrillic and hydrophilic surface. In one embodiment, the hydrated ECM is folded.

Kits for carrying out the methods of the invention, as well as methods for optimizing the cell culture conditions for culturing viable disease cells from a human primary cell sample are also encompassed by the invention.

The details of various embodiments of the invention are set forth in the description below. Other features, objects, and advantages of the invention will be apparent from the description and the drawings, and from the claims.

DETAILED DESCRIPTION

The present invention describes methods of preparing samples of viable diseased cells extracted from tissue specimens obtained from human subjects that are subsequently used while the cells are viable for clinical testing. These methods reduce the percentage of diseased (e.g. cancer) cells entering anoikis when human primary viable diseased cell samples are extracted from tissue, cultured, and prepared for testing. Research on anoikis to date has largely been aimed at harnessing the cellular apoptosis system to kill cancer cells while preserving healthy cell function. Anoikis research has not addressed the opposite function of temporarily suspending anoikis in order to attain a stable testable state of viable cultures of primary human cells, such as viable cancer cells from a tumor sample.

In order to obtain and test viable cells, they must first be isolated from tissue freshly removed from a patient. The present invention describes methods to suspend the anoikis processes initiated once cells are isolated from their native tissue so that it is possible to recover sufficient viable cells representative of their state in vivo. The present invention also describes methods to prepare a cell sample with physiological function and genomic composition comparable to the diseased cells when they were in vivo. The present invention also describes methods to prepare a cell sample that attaches to a culture surface in a manner that prevents the cell adhesion pathways from interfering with cell signaling pathway function. The methods of the invention involve the use of culture media comprising anoikis inhibitors and/or the use of anti-anoikis, stress-reducing atmospheric conditions and/or attachment of cells to anti-anoikis, stress reducing surfaces, and/or combinations thereof.

The utility and distinct advantages of the present invention are apparent by comparison of empirical results for different media with the present invention. Specifically, the present invention provides heterogeneous populations of cells capable of being cultured rapidly from milligram amounts of disease tissue to provide uniform clinical test results. Morphological and biomarker analysis of cells cultured using the compositions and methods of the present invention demonstrate the presence of multiple disease cell types (luminal, basal, stem, mesenchymal) replete with markers synonymous with disease (estrogen receptor, progesterone receptor, ErbB family receptors, CD10, claudin 4, CD49f, and other markers described herein) whereas other media known and commercially available in the art are incapable of generating suitable samples of diseased cells for clinical testing. Other media types do not support the propagation of luminal diseased cell types that also typically characterize diseased cell patient samples. Furthermore, other media types support only healthy cells or stem cells or squamous cell types that are not in keeping with the desired outcome of the present invention for a heterogeneous mixture of diseased cells from a patient sample. In summary the present invention provides cells of heterogeneous types with identified markers from a sample of primary diseased cells from a subject suitable for clinical testing whereas other media known in the art do not.

Various aspects of the invention are described further in the subsections below.

Inhibition of Anoikis

An obstacle to the successful culturing of primary cells, such as a sample of viable diseased cells from a subject such that the cells can be used in clinical testing, is anoikis, part of the natural control system in cells to program death. Programmed death may be initiated in response to many factors, potentially acting together, including, but not limited to, buildup of intolerable numbers of mutations, pH, cell age, environmental factors, various forms of stress such as high or low extremes of oxygen partial pressure, contact with cytokines, chemokines, cell signaling molecules, proteins, and various RNA, and cell growth beyond established tissue boundaries. Balance of programmed cell death activity is attained in cells by interlinked protein pathways that are either pro-anoikis or pro-angiogenic. For example, multi-domain pro-anoikis family members such as BAX and BAK, once activated, permeabilize mitochondria to trigger anoikis, whereas anti-anoikis BCL-2 family members preserve mitochondrial integrity. The BH3-only molecules (BH3s) promote anoikis by either activating BAX-BAK or inactivating anti-anoikis members.

Two forms of anoikis pathways have been described, intrinsic and extrinsic (see e.g., Fulda, S. and Debatin, K. M. (2006) *Oncogene* 7:4798-4811. The intrinsic anoikis pathway is characterized by mitochondrial membrane permeabilization, cytochrome c release, and apoptosome formation in response to cytotoxic stimuli. Extrinsic anoikis pathways are activated in response to ligand binding to death receptors of the TNF-superfamily. Exemplary ligands include TNFα and FasL. Death receptor activation can result in mitochondrial membrane permeabilizaton, cytochrome c release, and through caspase dependent cleavage and translocation of the pro-anoikis protein Bid to mitochondria, progress is made to later stages of anoikis. Both intrinsic and extrinsic pathways involve mitochondrial membrane permeabilization, cytochrome C release, and caspase activation as shared components.

Inhibition of anoikis in the present invention focuses on prevention and addressing the early, initiating, anoikis events for the sake of inhibition efficiency. Interruption of anoikis processes can be performed at later points before cell death and may also be desirable to revive cell culture samples that have already entered late stages of anoikis. Buffering of pH and redox potential and metal ion concentration (especially release of calcium) of the diseased primary cells are preferred early points of preventing anoikis. Early points of inhibition of anoikis preferably include disruption of mitochondrial permeability and inhibition of cytochrome c release. Somewhat later points of intervention in anoikis processes preferably include disruption of the caspase activity cascade and disruption of other proteases. Deregulated anoikis with increased expression of anti-anoikis molecules of the Bcl-2 family or reduction of pro-anoikis molecules such as Bax, Apaf-1 or caspase-8 are additional embodiments that may be combined to inhibit anoikis.

Accordingly, in the methods of the invention, a sample of viable diseased cells obtained from a subject is cultured in a media comprising at least one anoikis inhibitor. In certain embodiments, the culture media comprises at least one intrinsic anoikis inhibitor and at least one extrinsic anoikis inhibitor. In other embodiments, the media comprises at least one intrinsic anoikis inhibitor and at least one extrinsic anoikis inhibitor. In other embodiments, the apoptosis inhibitors are selected to agonize anti-anoikis pathways.

Following any initial preparatory steps on the tissue specimen to obtain cells suitable for culture (discussed further below), the cells extracted from the specimen are cultured in a media comprising anoikis inhibitors and more preferably a combination of anoikis inhibitors, most preferably combinations that are selected from intrinsic and or extrinsic pro-anoikis pathway inhibitors and or anti-anoikis activators.

Table 1 below shows non-limiting examples of general types of anoikis inhibitors and exemplary classes of inhibitors that fall within those types, as well as examples of specific reagents and whether the inhibitor affects the intrinsic anoikis pathway, the extrinsic anoikis pathway or a component common to both pathways (referred to herein as "shared pathway" anoikis inhibitors).

TABLE 1

Exemplary Anoikis Inhibitor Molecules

| General Inhibitor Type | Exemplary Classes | Specific reagent examples | Pathway |
| --- | --- | --- | --- |
| Kinase inhibitor | Rho-kinase inhibitor | Y-27632 | Shared |
|  | ALK5 inhibitor | Ceritinib, RepSox | Extrinsic |
| Protease inhibitor | Caspase inhibitor | Z-VAD-FMK | Shared |
|  | Matrix Metallo-Protease inhibitor | UK-356618 | Shared |
| Stress inhibitor | Redox buffering | Niacin | Intrinsic |
|  | Reactive Oxygen Species inhibitor | Glutathione ethyl ester | Intrinsic |
| Death Receptor inhibitor | TNF alpha | Infliximab | Extrinsic |
|  | TGF beta | Fresolumimab | Extrinsic |
| Cytochrome C inhibitor | Release inhibitor | Melatonin | Shared |
|  | Carbonic anhydrase antagonist without $Ca^{2+}$ channel activation | Methazolamide | Shared |

TABLE 1-continued

Exemplary Anoikis Inhibitor Molecules

| General Inhibitor Type | Exemplary Classes | Specific reagent examples | Pathway |
|---|---|---|---|
| Adhesion-related anoikis inhibitor | Integrin stabilizer Integrin ligand | Tetraiodothyronine Fibrinogen, fibronectin | Extrinsic Extrinsic |

In one embodiment, the at least one anoikis inhibitor is a Rho-associated kinase inhibitor, non-limiting examples of which include Y-27632, GSK429286A and RKI-1447. In one embodiment, the at least one anoikis inhibitor is a caspase inhibitor, such as a pan caspase inhibitor (e.g., Z-VAD-FMK), a caspase 3 inhibitor (e.g., Z-DEVD-FMK, Q-VD-OPh), a caspase 8 inhibitor (e.g., Z-IETD-FMK, Ac-LETD-CHO, Q-VD-OPh) and/or a caspase 9 inhibitor (e.g., Z-LEHD-CHO, Ac-LETD-CHO, Q-VD-OPh). In one embodiment, the at least one anoikis inhibitor is a cytochrome C inhibitor, non-limiting examples of which include melatonin and methazolamide. In one embodiment, the at least one anoikis inhibitor is a Matrix Metalloprotease (MMP3) inhibitor, a non-limiting example of which is UK-356618. In one embodiment, the at least one anoikis inhibitor is an ALK5 inhibitor, non-limiting examples of which include ceritinib, RepSox, alectinib, AP26113, GW788388, SD-208 and Galunisertib (LY2157299). In one embodiment, the at least one anoikis inhibitor is a TNFα inhibitor, non-limiting examples of which include R-7050, infliximab, golimumab, adalimumab, certolizumab and etanercept. In one embodiment, the at least one anoikis inhibitor is a TGFβ inhibitor, non-limiting examples of which include fresolimumab, as well as inhibitors of TGFβ pathway signaling, such as ceritinib, RepSox, alectinib, AP26113, GW788388, SD-208 and Galunisertib (LY2157299). In one embodiment, the at least one anoikis inhibitor is an oxidative stress reducer (i.e., a Reactive Oxygen Species inhibitor), non-limiting examples of which include glutathione, glutathione ethyl ester, methionine, cystine, cysteine, glutamic acid and glycine. In one embodiment, the at least one anoikis inhibitor is a redox buffering agent, non-limiting examples of which include niacin, niacin-related compounds, calciferols, beta carotene and vitamin C. In one embodiment, the at least one anoikis inhibitor is an adhesion-related anoikis inhibitor, non-limiting examples of which include fibrinogen, fibronectin, and tetraiodothyronine. In one embodiment, the at least one anoikis inhibitor is a Fas and/or FasL inhibitor, non-limiting examples of which include triiodothyronine and tetraiodothyronine. In one embodiment, the at least one anoikis inhibitor is a Bax inhibitor, non-limiting examples of which include Bax inhibitor-1 and V5 peptide. In one embodiment, the at least one anoikis inhibitor is an Apaf-1 inhibitor, non-limiting examples of which include QM31 and minocycline.

In other embodiments, cells are cultured with two or more anoikis inhibitors, such as with two, three, four, five, six, seven, eight, nine or ten anoikis inhibitors. Any of the aforementioned anoikis inhibitors can be used in combination. For example, in one embodiment, the cells are cultured with a Rho-associated kinase inhibitor and a caspase inhibitor. In another embodiment, the cells are cultured with a Rho-associated kinase inhibitor and an MMP3 inhibitor. In another embodiment, the cells are cultured with a caspase inhibitor and an MMP3 inhibitor. In another embodiment, the cells are cultured with a Rho-associated kinase inhibitor, a caspase inhibitor and an MMP3 inhibitor. In another embodiment, the cells are cultured with a Rho-associated kinase inhibitor, a caspase inhibitor, an MMP3 inhibitor and a Death Receptor inhibitor (e.g., a TNFα inhibitor, a TNFR1 inhibitor, a TGFβ inhibitor, an ALK5/TGFBR1 inhibitor, a Fas inhibitor or a FasL inhibitor). In another embodiment, the cells are cultured with each of: a kinase inhibitor, a protease inhibitor, a stress inhibitor, a Death Receptor inhibitor, a cytochrome C inhibitor and an anoikis inhibitor, non-limiting examples of which include the reagents set forth in Table 1 and listed above. Other suitable combinations of anoikis inhibitors can be determined using the guidance provided herein (e.g., see Examples 3-5).

Inhibitors typically are added to the culture media at a concentration of 0.001-0.1 micromole per 100,000 cells, preferably at 0.01-0.1 micromole per 100,000-10,000,000 cells, depending upon the amount of cells in a diseased cell sample.

In certain embodiments, use of a single anoikis inhibitor in the culture media provides benefit to certain cell types. However, in specific embodiments, it is the benefit of combining the intrinsic, extrinsic, and anoikis inhibition components that provides the most optimal conditions for preparing the sample for clinical testing. It has been observed that this combination of anti-anoikis components renders a heterogeneous population of diseased cells from a significant majority of specimens from different patients suitable for clinical testing of viable diseased cells. Each patient specimen may enter anoikis for any of a number of different individual or combined reasons described previously, each with the ability to rapidly and catastrophically make the specimen un-useful for any kind of viable cell test. Only through the significant attenuation of a combination of these routes to anoikis can the sample of heterogeneous diseased cells be made stable upon removal from tissue for viable cell testing. Clinical testing requires that most samples that are received for testing reliably provide a physician with test result information to guide the treatment of their patients. The present invention provides the means of accomplishing this requirement.

Anti-Anoikis Atmospheric Conditions

Another factor affecting whether a primary cell cultured in vitro enters anoikis has been found to be the atmospheric conditions under which the cells are cultured. It has now been discovered that combining the use of at least one anoikis inhibitor in the media with culture under conditions of greater than 2% and less than 20% oxygen serves to further inhibit anoikis of primary cells in the sample of viable diseased cells. While not being bound by mechanism, it is thought that culturing the cells in atmospheric conditions of greater than 2% and less than 20% oxygen reduces anoikis associated with oxidative stress. In another embodiment, the cell sample is maintained in atmospheric conditions that permit glycolysis and mitochondrial function conducive to cell proliferation. In a more preferred embodiment, the cell culture is maintained in atmospheric conditions that balance the reduction in anoikis associated with oxidative stress and the requirement for oxygen conducive to cell proliferation. A most preferred embodiment is to maintain the cell sample in atmospheric conditions comprising 6%-17% oxygen, a range variant that is between the hypoxic conditions the cells experience in vivo (1-5% oxygen) and the normoxic conditions the cells experience when exposed to the atmosphere (20% oxygen). In another embodiment, the cells are cultured under conditions comprising 10% oxygen. In yet other embodiments, the cells are cultured under conditions comprising 6-9% oxygen, 9-11% oxygen, 8-12% oxygen, 7-13% oxygen, 6-14% oxygen, 11-13% oxygen, 13-15% oxygen, 15-17% oxygen, 9-15% oxygen, 6% oxygen, 7% oxygen, 8% oxygen, 9% oxygen, 11% oxygen, 12% oxygen, 13% oxygen, 14% oxygen, 15% oxygen, 16% oxygen or 17% oxygen. In another embodiment, cells cultured under conditions comprising 1-5% oxygen.

In certain embodiments, cells are cultured under two or more different atmospheric conditions for different periods of time. For example, the cells can first be cultured under conditions comprising 6-17% oxygen (e.g., 10% oxygen) and then cultured under conditions comprising 1-5% oxygen, or comprising 17-19% oxygen or comprising 18-20% oxygen or comprising 20% oxygen.

Other aspects of the atmospheric conditions and temperature for cell culture are those typically used for culture of mammalian (e.g., human cells). For example, the cells typically are cultured in atmospheric conditions comprising at least 5% carbon dioxide, relative humidity (RH) between 40%-100% (e.g., 85% RH) and at a temperature of 37° C.

Surface Attachment and Inhibition of Anoikis

Most non-transformed and many cancer epithelial cell types undergo anoikis when they lose their contact with the hydrated extracellular matrix (ECM), a phenomenon termed adhesion-related anoikis. Maintenance of the structural and functional integrity of the epithelial cell requires highly dynamic cell-cell and cell-matrix interactions involving different types of surface receptors. Among these receptors are adhesion molecules, such as cadherins and integrins, which play a major role by recognizing and interacting with other cell adhesion receptors on neighboring cells and by binding components of the ECM. Besides providing mechanical anchorage to the cell, these structures also are of functional importance; they transduce signals from the ECM and neighboring cells that are critical for survival and proliferation. The composition, patterning, and structural nature of the ECM has been demonstrated to be critical in restoring and or establishing the viability of mammalian cells. Reduction or loss of these contacts or signals or their integrity frequently initiates anoikis.

Reduction of anoikis for epithelial cells is critical to preparing uniform samples of viable diseased cells, especially for clinical test purposes. Adhesion-related anoikis is a form of anoikis that is initiated in vivo by anchorage-dependent cells such as epithelial cells, becoming detached from the surrounding tissue extracellular matrix (ECM). Usually cells stay close to the tissue to which they belong since the communication between proximal cells as well as between cells and ECM provides essential signals for growth or survival. When cells are detached from the ECM, there is a loss of normal cell—matrix interactions, which leads to forms of intrinsic and extrinsic anoikis. By their very nature, diseased cells often have heterogeneous attachment stability. In cancer, poor attachment is characterized pathologically as metastasis, a highly fatal form of the disease. Preparation of uniform samples of diseased cells for clinical testing necessary involves their removal from their ECM in their native environment, which therefore can induce anoikis.

Therefore, various embodiments of the methods of the present invention replace the ECM from which the cells were removed with an in vitro ECM that restores cell-cell and cell-ECM contacts, thereby inhibiting or reducing anoikis. Furthermore, one or more components can be added to the culture media to promote restoration and/or activation of cell-cell and or cell-ECM adhesion and to prevent anoikis.

Accordingly, certain embodiments of the methods of the invention include use of a culture media comprising at least one component that promotes restoration and or activation of cell-cell and or cell-ECM adhesion and prevents anoikis. The adhesion pathway activators that prevent this form of anoikis activity can be selected from a group consisting of but not limited to $Ca^{2+}$, $Mg^{2+}$, $Mn^{2+}$, triiodothyronine, tetraiodothyronine, fetuin, solution forms (e.g. fibrinogen) or coatings of extracellular matrix components or combinations of such components such as fibronectin, collagens, laminins, vitronectin, intercellularCAMs, VascularCAMS, MAdCAMS, glycosaminoglycans, proteoglycans or derivatives and or peptides thereof. Growth factors such as EGF to increase focal adhesion kinase activity and counteract PTEN anoikis promotion following integrin disruption are also included in the present invention.

In certain embodiments, two or more of the above components that inhibit anoikis can be used in the culture media. For example, in one embodiment, the sample of viable diseased cells is cultured in a media comprising at least one intrinsic anoikis inhibitor and at least one extrinsic anoikis inhibitor.

In further embodiments, the viable cell sample is attached to a culture surface, such as a culture vessel (e.g., culture plates divided up into wells, T25, T75, and T150 flasks, multilevel culture vessels and the like) or a test surface (e.g., a biosensor surface) via an extracellular matrix. In other embodiments, the viable cell sample is attached to a cell culture vessel or test surface via a hydrated ECM where the ECM retains sufficient water such that the ECM is fully wetted and is never allowed to dehydrate prior to use. In additional embodiments, the viable cell sample is attached to a cell culture vessel or test surface via a hydrated and folded ECM whereby the ECM is comprised of an ordered, structured, and reproducible arrangement of its protein component(s). In embodiments, the cell sample of viable cells is attached to a fibrillic and hydrophilic combined collagen and fibronectin surface prepared to maintain these proteins' natural in vivo-like structures that can be recognized by specific integrins and or promote cell-cell interactions via for example cadherins or adherins. In certain embodiments, the collagen and fibronectin are formed into hydrophilic fibrils and the two-protein interaction is comprised of specific amino acid sequence binding sites. In embodiments, the cell-ECM attachment forms a collagen—laminin 332 co-structure. Laminin 332 is also known as laminin V and in certain embodiments can be used as a single ECM on the culture surface. In some embodiments, the surface to be coated with ECM is plastic, glass, or especially glass imprinted with gold electrodes, or titanium coated plastic, or optically active metal coated glass or plastic formed into a wave-guide, gold coated glass. Other preferred embodiments the surface to be coated with ECM is a biosensor for clinical test purposes.

In each of the embodiments involving surface attachment, the surface coating is prepared using standard methods known to those skilled in the art. For example, methods of preparing a hydrated ECM or a hydrated and folded ECM are well established in the art (see e.g., Anderson, D. G. et al. (2004) *Nat. Biotechnol.* 22:863-866; Flaim, C. J. et al. (2005) *Nat. Methods* 2:119-125; Falsey, J. R. et al. (2001) *Bioconjug. Chem.* 12:346-353; Kuschel, C. et al. (2006) *Biotechniques* 40:523-531; Reticker-Flynn, N. E. et al. (2012) *Nat. Commun.* 3:1122).

In other embodiments, the cell attachment to a surface is optimized to ensure that the level of cell attachment is not driven by conditions that stress the cells or conditions that increase anoikis, which may result in cell attachment that interferes with cell signaling activity. In other embodiments, the cell attachment to the surface is optimized to ensure that extracellular coating and adhesion mechanism are matched to the signaling pathway of interest.

Accordingly, in certain embodiments, the methods of the invention for preparing primary cells for conducting a clinical test comprises inclusion of step comprising attaching the sample of cells to a surface comprising a hydrated extracellular matrix (ECM). In one embodiment, the ECM consists of fibronectin and collagen. In one embodiment, folded ECM is used. In another embodiment, fibronectin and collagen comprise a fibrillic and hydrophilic surface. In one embodiment, the ECM consists of a fibrillic and hydrophilic collagen-laminin 332 (laminin V) co-structure. In another embodiment, the ECM consists of laminin 332 (laminin V). The invention provides a method of preparing primary cells for conducting a clinical test, the method comprising:

attaching the sample of viable diseased cells to a biosensor surface comprising a hydrated extracellular matrix (ECM), or a hydrated and folded ECM, wherein the ECM consists of: (i) fibronectin and collagen; (ii) collagen and laminin 332 (laminin V) or (iii) laminin 332 (laminin V); and conducting a clinical test using a biosensor on the sample of viable diseased cells.

In certain embodiments, the sample of viable diseased cells may be attached to two or more different surfaces at different time periods. For example, the cells initially may be attached to a cell surface such as a culture plate, culture flask or other culture vessel comprising an anti-anoikis, stress-reducing ECM as described above and cultured for a period of time. Then, the cells may be detached from this surface (e.g., as described further below) and subsequently attached to another surface, such as a biosensor surface for clinical testing. This biosensor surface also can comprise an anti-anoikis, stress-reducing ECM as described above.

Use of Multiple Culturing Conditions in Combination

Regulation of in vivo cell viability and function is known to be highly complex, relying upon multiple signal inputs and responses to maintain stable cellular processes. This is especially true for the effect the cell microenvironment has on cells. Culturing human primary cells in the laboratory setting has been characterized by failure and a prevailing mindset that highly reproducible primary tissue culturing is not possible, especially of diseased cells. This mindset has also blocked the development of any live primary cell functional clinical test to date. Weighing heavily on this history of failure has been the lack of consideration of the need to address the multiple signal inputs and responses required by primary cells to establish a viable culture ex vivo. When different diseased cells are cultured ex vivo, they will undergo anoikis as their natural regulatory control signaling is disrupted. In order to overcome this regulatory control for the preparation of diseased cells for clinical testing, a combination of methods is required to address the regulatory signal maintenance requirement and prevent anoikis. The methods of the invention for preparing primary cells encompass the use of multiple different culture media and/or culture conditions that are used in combination to prepare the primary cells for clinical testing. The use of different culture media and/or culture conditions in combination further improves the preparation of the primary cells such that sufficient numbers of cells are obtained in a sufficient period of time, while maintaining the physiological and genomic characteristics of the cells, such that they provide reliable results in clinical testing.

In certain embodiments, the cell sample is cultured first in a media comprising anoikis inhibitor(s) and then subsequently cultured in a media that does not include anoikis inhibitor(s). In certain embodiments, the cell sample is maintained first in an atmosphere comprising greater than 2% and less than 20% oxygen (e.g., greater than 3% and less than 19% oxygen, 6-17% oxygen, 10% oxygen, or any of the other atmospheric conditions described herein above 2% and below 20%) and subsequently maintained in an atmosphere comprising 20% oxygen. In certain embodiments, the period of time the cell sample is cultured in a media comprising anoikis inhibitor(s) ranges from 1-10 hours, from 10-20 hours, from 20-30 hours, from 30-40 hours, from 40-50 hours, or more than 50 hours. For example, the cell sample can be cultured in a media comprising anoikis inhibitor(s) for at least 12 hours, at least 24 hours, at least 48 hours, at least 96 hours, at least 120 hours, 24-48 hours, 24-96 hours, or 24-120 hours. In certain embodiments, the period of time the cell sample is maintained in an atmosphere with greater than 2% and less than 20% oxygen ranges from 1-10 hours, from 10-20 hours, from 20-30 hours, from 30-40 hours, from 40-50 hours, or more than 50 hours. For example, the cell sample can be maintained in an atmosphere with greater than 2% and less than 20% oxygen for at least 12 hours, at least 24 hours, at least 48 hours, at least 96 hours, at least 120 hours, 24-48 hours, 24-96 hours, or 24-120 hours.

In other embodiments, the cell sample is maintained in an atmosphere comprising greater than 2% and less than 20% oxygen for a period of time after the cells are transferred from one culture vessel to another vessel. In certain embodiments, the period of time the cell sample is maintained in an atmosphere comprising greater than 2% and less than 20% oxygen after the cells are transferred from one culture vessel to another vessel ranges from 1-10 hours, from 10-20 hours, from 20-30 hours, from 30-40 hours, from 40-50 hours, or more than 50 hours. A preferred embodiment is to culture the cell sample in atmospheric conditions comprising 6%-17% oxygen after the cells are transferred from one culture vessel to another vessel. In certain embodiments, the atmospheric conditions maintained after the cell sample is transferred to a new culture vessel comprise oxygen that ranges between 1-5%, 6-9%, 9-11%, 8-12%, 7-13%, 6-14%, 11-14%, 14-17%, or 17%-20% or conditions of 6%, 7%, 8%, 9%, 10%, 11%, 12%, 13%, 14%, 15%, 16% or 17% oxygen. In embodiments, the cell sample is maintained first in an atmosphere comprising greater than 2% and less than 20% oxygen after the cells are transferred from one culture vessel to another culture vessel and subsequently placed in an atmosphere comprising 20% oxygen.

In other embodiments, the cell sample is cultured in a media comprising anoikis inhibitor(s) for a period of time after the cells are transferred from one culture vessel to another vessel. In certain embodiments, the period of time the cell sample is cultured in a media comprising anoikis inhibitors after the cells are transferred from one culture vessel to another vessel ranges from 1-10 hours, from 10-20 hours, from 20-30 hours, from 30-40 hours, from 40-50 hours, or more than 50 hours. In embodiments, the cell sample is cultured first in a media comprising anoikis inhibitor(s) after the cells are transferred from one culture vessel to another culture vessel and subsequently placed in a culture media that does comprise anoikis inhibitor(s).

In certain embodiments, cells are cultured in a base media supplemented with various components. In one embodiment, the base media is a serum free base media. In another embodiment, the base media comprises anoikis inhibitor(s) as described herein and may contain additional components serving additional functions as described below. Non-limiting examples of base media that are serum-free that could be modified by addition of components described herein include DMEM, F12, 50% DMEM/50% F12, MEGM, MCDB-170.

In other embodiments, the cells are cultured in serum free culture media comprising at least one component that promotes growth, division, or cell cycling to facilitate cell proliferation. The media containing this type of component can be the same media that contains the anoikis inhibitor(s) or can be a different media into which the cells are transferred. Non-limiting examples of such components that promote growth, division, or cell cycling to facilitate cell proliferation include growth factors associated with the tumor microenvironment, HGF, FGF (types 1-4), exosomes, miRNAs, other small non-protein coding RNAs, longer non-protein coding RNAs, hormones, IGF, VEGF, EGF, interleukins, cytokines, chemokines, and other factors such as may be known as autocrine or paracrine factors produced by cells in and around the diseased cells.

In other embodiments, the culture media is comprised of at least one component that promotes temporary reversal of adhesion activity to facilitate gentle transfer of a cell culture from one vessel to another vessel. The media containing this type of component can be the same media that contains the anoikis inhibitor(s) or can be a different media into which the cells are transferred. Non-limiting examples of such components that promote temporary reversal of adhesion activity to facilitate gentle transfer of a cell culture from one vessel to another vessel include non-enzymatic and enzymatic treatments, $Ca^{2+}$, $Mg^{2+}$, and or $Mn^{2+}$ chelators such as EGTA, EDTA, and other divalent metal ion chelators known to those practiced in the art, and additionally dispase, TrypLE, trypsin, accutase, accumax, collagenase, hyalronidase, elastase, trypsin inhibitor, STEMxyme, pronase, deoxyribonuclease. Combinations of the members of this group at differential concentrations, applied for different amounts of time at different temperatures are included in the present embodiment.

In other embodiments, the culture media is a serum-free culture base media comprising at least one component that preserves the physiological or genomic characteristics of the diseased cells. The media containing this type of component can be the same media that contains the anoikis inhibitor(s) or can be a different media into which the cells are transferred. Non-limiting examples of such components that preserve the physiological or genomic characteristics of the diseased cells include essential and non-essential amino acids, vitamins, especially B vitamins, rare essential metals, pH buffer(s) (e.g. N-[2-HydroxyEthyl] Piperazine-N'-[2-EthaneSulfonic acid] also known as HEPES, $NaHPO_4$, $NaH_2PO_4$), salts (Na+, K+, Fe, Zn, Cu, $Mg^{2+}$, $Ca^{2+}$, $Mn^{2+}$, Cl, $CO_3$, $SO_4$), selenites, silicates, glucose or sugars or other biologically practical carbon sources, lipids, fatty acids such as lipoic acid, pyruvate, BSA (e.g also includes reagents such as Albumax or other serum albumins), transferrin, growth factors, chemokines, cytokines, mitogens, ethanolamine, phosphoethanolamine, albumins, hormones (e.g. progesterone, testosterone, estradiol—especially 17β-estradiol, hydrocortisone, insulin), putrescine, pyruvate, thymidine, linoleic acid, folic acid, folinic acid, choline, pyridoxal hydrochloride, biotin, hypoxanthine, purine and purine derivatives, pyrimidines and pyrimidine derivatives, antibiotics, anti-fungals, anti-mycotics. The media components can be selected to support diseased epithelial cell growth and said selected components can cause separation from the growth of healthy, disease-free, epithelial cells. Growth factors, cytokines, and chemokines are added at 0.001-0.1 nmol per 100,000 cells, preferably at 0.01-0.1 nmol per 100,000-1,000,000 cells, depending upon the amount of cells in a diseased cell sample.

In one embodiment of a combination method of the invention for preparing a sample of viable diseased cells obtained from a human subject for clinical testing, the method comprises:
    culturing the sample of viable diseased cells obtained from the human subject in a media comprising at least one inhibitor of an intrinsic anoikis pathway and at least one inhibitor of an extrinsic anoikis pathway under conditions comprising 6-17% oxygen (e.g., 10% oxygen); and
    conducting a clinical test on the sample of viable diseased cells.

In another embodiment of a combination method of the invention for preparing a sample of viable diseased cells obtained from a human subject for clinical testing, the method comprises:
    culturing the sample of viable diseased cells obtained from the human subject in a media comprising at least one digestion enzyme and at least one anoikis inhibitor under conditions comprising 6-17% oxygen (e.g., 10% oxygen), for example for at least one hour (e.g., 1-3 hours, 3 hours or no more than 3 hours);
    culturing the sample in a media comprising at least one anoikis inhibitor and lacking digestion enzymes under conditions comprising 6-17% oxygen (e.g., 10% oxygen), for example for at least 10 hours, or at least 24 hours, or at least 48 hours or least for 96 hours, or at least 120 hours, or for 24-48 hours, or for 24-96 hours or for 24-120 hours; and
    culturing the sample in media lacking anoikis inhibitors under conditions comprising 20% oxygen, to thereby prepare the sample for clinical testing.

In another embodiment of a combination method of the invention for preparing a sample of viable diseased cells obtained from a human subject for clinical testing, the method comprises:
    culturing the sample of viable diseased cells obtained from the human subject in a media comprising at least one inhibitor of an intrinsic anoikis pathway and at least one inhibitor of an extrinsic anoikis pathway under conditions comprising 6-17% oxygen (e.g., 10% oxygen); and
    attaching the sample of viable diseased cells to a surface comprising a hydrated extracellular matrix (ECM), wherein the ECM consists of: (i) fibronectin and collagen; (ii) collagen and laminin 332 (laminin V) or (iii) laminin 332 (laminin V).

In one embodiment, the surface to which the sample of viable diseased cells is attached is a biosensor surface, the method further comprising conducting a clinical test using a biosensor on the sample of viable diseased cells.

In another embodiment of a combination method of the invention for preparing a sample of viable diseased cells obtained from a human subject for clinical testing, the method comprises:
    culturing the sample of viable diseased cells obtained from the human subject in a media comprising at least one anoikis inhibitor under conditions comprising 6-17% oxygen (e.g., 10% oxygen);
    attaching the sample of viable diseased cells to a surface comprising a hydrated extracellular matrix (ECM) consisting of fibronectin and collagen; and continuing culture of the sample attached to the surface in a media comprising at least one anoikis inhibitor under conditions comprising 6-17% oxygen (e.g., 10% oxygen).

In one embodiment, the sample is cultured with at least one inhibitor of an intrinsic anoikis pathway and at least one inhibitor of an extrinsic anoikis pathway. In one embodiment, the surface to which the sample of viable diseased cells is attached is a biosensor surface, the method further comprising conducting a clinical test using a biosensor on the sample of viable diseased cells.

In yet another embodiment of a combination method of the invention for preparing a sample of viable diseased cells obtained from a human subject for clinical testing, the method comprises:

culturing the sample of viable diseased cells obtained from the human subject in a media comprising at least one digestion enzyme (e.g., collagenases and hyaluronidase) and at least one anoikis inhibitor (e.g., an intrinsic anoikis inhibitor(s) and/or an extrinsic anoikis inhibitor(s)) under conditions comprising 6-17% oxygen (e.g., 10% oxygen) for no more than three hours;

plating the sample of viable diseased cells onto a cell culture vessel surface comprising a hydrated and folded extracellular matrix (ECM) consisting of human collagen I and human fibronectin and culturing in a media comprising at least one anoikis inhibitor (e.g., an intrinsic anoikis inhibitor(s) and/or an extrinsic anoikis inhibitor(s)) under conditions comprising 6-17% oxygen (e.g., 10% oxygen); and culturing the sample in a serum free base media until a clinical test on the viable disease cells is performed or until 50%-80% confluency of the viable disease cells is attained.

This combination method can include additional steps after the last culturing steps. For example, in one embodiment, the primary cells are harvested by culture of the cells in a media comprising at least one component that promotes temporary reversal of adhesion activity (e.g., minimal enzyme and divalent metal ion conjugating media) for no more than 10 minutes, under conditions that reverse attachment of the viable disease cells to the surface without damaging the adhesion components of the cell. In another embodiment, the combination method can further comprise transfer of the harvested cells to a surface (e.g., a second culture vessel, or a biosensor surface) comprising a hydrated and folded extracellular matrix (ECM) (e.g., consisting of human collagen I and human fibronectin) and culture in a media comprising at least one anoikis inhibitor under conditions comprising 6-17% oxygen (e.g., 10% oxygen) for at least 1-8 hours, e.g., until significant attachment and spreading is observed.

Following culture of primary cells according to the methods of the invention for preparing the cells for clinical testing, the methods can also include identification and characterization of diseased cell populations. In one embodiment, diseased cell populations are identified and/or characterized by detection of specific markers, such as those listed in Table 2, e.g, by FACS or by qPCR methods. Additionally, or alternatively, diseased cell populations can be identified and/or characterized by testing of adhesion and/or cell signaling pathway activity, e.g., using a biosensor.

Cell Samples and Initial Preparation Thereof

The methods of the invention can be applied to a wide variety of primary cells, in particular primary human cells, in particular viable diseased cells from a human subject. In on embodiment, the cells are cancer cells from a tumor sample.

In embodiments, the cell sample is extracted from a fresh solid cancer tissue specimen obtained from a core needle biopsy, fine needle aspiration, vacuum-assisted core biopsy, image-guided core needle biopsy, surgical biopsy, surgical resection, or any other suitable medical procedure.

In embodiments, the cell sample is obtained from any biological tissue or fluid type, either diseased or normal.

In preferred embodiments, diseased epithelial cells may be derived from breast tissue, stomach tissue, colon/intestinal tissue, lung tissue, head tissue, neck tissue, parotid tissue, ovarian tissue, uterine tissue, cervical tissue, prostate tissue, pancreatic tissue, kidney/renal tissue, or bone and/or bone marrow. In specific embodiments, the tissue is derived from patients with the canonical breast cancer pathological types—for example those described by clinical pathological markers: ER+/HER2−, ER+/HER2+, ER−/HER2+, ER−/HER2.

In embodiments, culture media comprised of different components or different concentrations of components are used at different stages of cell preparation. In embodiments, the cell sample is prepared using one, two, three, four or more than four different culture media. In embodiments, the cell sample is maintained in atmospheric conditions comprised of different concentrations of oxygen at different stages of cell preparation. In embodiments, one, two, three, four or more than four different atmospheric conditions are used at different stages of cell preparation. In other embodiments, different culture media, and anoikis inhibitors, and atmospheric conditions, and attachment conditions are used together in any combination.

To prepare a diseased cell sample, a tissue specimen typically is first mechanically divided into smaller pieces and placed in a digestion media containing enzymatic agents known to digest tissue (i.e., digestion enzymes) without causing anoikis, cell surface adhesion molecule damage, or other non-anoikis means of cell death. Accordingly, in certain embodiments, after obtaining the sample from the subject, the sample of viable diseased cells is contacted with a digestion media comprising one or more enzymatic agents for a period of time, wherein the digestion media digests tissue without causing anoikis, cell surface adhesion molecule damage or non-anoikis means of cell death. The enzymatic agents can be selected from the following non-limiting examples: collagenases of any of the known types, hyalronidases, papain, dispase, elastase, trypsin and any combinations thereof. In one embodiment, the digestion media comprises a mixture of collagenases and hyaluronidase. When used in combination, the enzymatic agents may be used in different ratios to optimize yield and reduce damage to the cells. The tissue specimen may be placed in a digestion media comprised of any of the agents above for different periods of time, including minutes up to several days. In most preferred embodiments, the enzymatic agents are selected to limit the exposure time of the cells to the enzymes and optimize the yield of a heterogenous population of viable cells.

In other embodiments, the digestion media is supplemented with at least one anoikis inhibitor. A preferred embodiment is to supplement the digestion media with at least one anoikis inhibitor directed at intrinsic anoikis pathway induction and at least one inhibitor directed at extrinsic pathway induction. The digestion media also can be supplemented with at least one anoikis inhibitor. A further embodiment is to use any anoikis inhibitor or combination of anoikis inhibitors on a continuous or intermittent basis during the extraction process. In one embodiment, after obtaining the tissue sample from the subject, the cells are cultured in a media containing at least one digestion enzyme (e.g., collagenases and hyaluronidase) and containing at least one anoikis inhibitor, preferably under conditions of greater than 2% and less than 20% oxygen (more preferably at 6-17% oxygen, more preferably at 10% oxygen). The cells are cultured in this media for a period of time (e.g., at least one hour, at least two hours, at least three hours or for one to five hours or for three hours), and then the cells are cultured in the same media (i.e., comprising anoikis inhibitor(s)) but without the digestion enzymes.

Determination that the diseased cells of interest are present when practicing the composition or methods of the present invention may be made by examining expression of markers that identify particular cell types. Non-limiting examples of markers for cell type identification include those listed in Table 2 below. Use of one or more markers specific for the general cell type or for the disease of interest, keeping in mind that there is heterogeneity of the sample in many cases, is most desirable. Marker expression characterization, quantification, or presence, can be made by examining the protein, mRNA level, other smaller RNA levels (e.g. siRNA, lncRNA, microRNA, regulatory RNA) by for examples FACS, quantitative or other PCR methods, mass spectroscopy, or polyacrylamide gels.

TABLE 2

Exemplary Markers for Cell Identification in Primary Cell Samples

| Marker Name | Cell Type | Marker Name | Cell Type |
| --- | --- | --- | --- |
| ESR1 | disease | CD49F/ITGA6 | Stem, epithelial |
| PGR | disease | Claudin4 | Stem, mesenchymal epithelial |
| HER2 | disease | MME/CD10 | Luminal epithelial |
| Keratins 8, 18, 19 | Luminal epithelial | CYP2b7P1, TFF1, AGR3, FOXA1 | ER+ breast disease epithelial, disease |
| beta-catenin | | | |
| Keratins 5, 14 | Basal epithelial | Smooth muscle actin, CALLA | Myo-epithelial |
| E-cadherin, EpCam | epithelial | A2ML, FABP7, ACE2, HORMAD1 | Triple negative cancer or disease |
| ErbB family | disease | TFF1 | disease |
| IGFr, c-myc, VEGFr | disease | K19, CD44 | Stem, disease |

Transformation of cells may be desirable for working with certain primary cell materials to meet other research or commercial goals unrelated to the present invention. Since transformation of primary cells potentially creates a cell state that is not representative of the in vivo tumor functional activity, the present invention excludes cell transformation that modifies the genetic, epi-genetic, or disease function of the cells such that the in vivo state is not present.

Additionally, tumorigenicity in mouse models has become a standard for determining the presence of cancer cells in an isolated cell sample. Notwithstanding the considerable effort and knowledge that has been gained through such experimentation, the present invention recognizes that many intrinsic tumor types have not reached acceptable levels of reliable recapitulation of the in vivo disease and consistency of growth in the mouse to be useful in clinical practice with patients. Many tumor types will not grow reliably in mice; the mouse is different from humans in fundamental ways at the cellular level (e.g. critical proteins may have the same name in both mammals but have different sequences, structures, functions, and location that change and affect function of the cellular pathways); and the amount of time to get sufficient mouse xenograft material does not meet the time requirement for useful clinical test results. As such, xenograft models as means to testing or providing useful cells for clinical testing lie outside the present invention.

In an embodiment, the preparation of the cell sample takes place at the location where the clinical testing will be performed (e.g., laboratory, hospital). As such, the cells can be preserved in a well-known transfer medium to bridge the time from removal from the subject to initiation of the cell sample preparation methods described herein. In another embodiment, the preparation of the cell sample takes place at a different location than where the specimen is removed from the patient requiring shipment of the specimen in a specimen collection kit. The time required to ship the specimen to the location where the cell sample will be prepared can range from 1-36 hours, and more than 36 hours.

Preparation of Culture Media

Culture media for use in the methods of the invention can be prepared by standard methods in which components are added to a base media at the desired concentration. The preparation of culture media for use in the present invention can be made by the addition of individual components in liquid or solid form, in aqueous or organic solutions (preferably at not more than 0.3% final organic solvent composition). Components may be combined before final preparation of the working medium to make bullet concentrated stock solutions for storage and for ease and uniformity of preparation. In the case of the use of bullet concentrated stock solutions for the practice of the present composition or methods, reagents are preferably combined by aqueous solubility level, i.e. salts and more water-soluble components are stored as an aqueous bullet type and less water-soluble, hydrophobic, components are stored as an ethanol, dimethylformamide, and or dimethysulfoxide stock. The composition comprising the stock solutions of non-proteinaceous components may be stored ideally −30° C. to −80° C. in a sealed, light-proof container to prolong their useful life time.

Culture media comprising one or more anoikis inhibitors (optionally including other components as described above) can be further conditioned in advance of application onto the sample of viable disease cells by placement in environmental conditions of 10% $O_2$, 5% $CO_2$, 37° C., so as to further reduce the potential anoikis effect on cells.

In all embodiments, the medium is used in a sterile or essentially aseptic form. This form may be created by various methods known to those skilled in the art but preferably is performed in a manner that is non-destructive to the composition and or individual components. For example, a preferable method is filter sterilization using a low protein-binding membrane filter 0.1-1.0 micrometer pore size.

In embodiments, apparent to one of ordinary skill in the art, the concentration of a given component can be increased or decreased beyond the range listed in the included tables and the effect of the increased or decreased concentration can be determined using routine empirical experimentation. The optimization of the present media formulations for any specific diseased cell or tissue type can be carried out using empirical approaches for examples such as titration, addition, deletion, or Design of Experiment (DOE), or combinations of these.

Optimization of Culture Conditions

To optimize the cell preparation conditions, which includes composition of the media, the concentration of the media components, the length of time the culture media or atmospheric conditions are used, the stages/steps of processing the conditions are applied, the different types of culture media used, or the type of surface the cells are attached to, a series of experiments can be conducted to evaluate the cell expansion rate, the type of viable cells in the cell sample, the proportion of cell types in the cell sample that result, whether or not the cells attach to a surface, the viability of the cells, the mitochondrial activity of the cells, or any other measurement of cell preparation results under any combinations of these conditions. The results from these experiments can be used to select the cell preparation conditions that are optimal for the requirements of a particular clinical test, or disease, or cell type, or tissue type.

Other suitable optimization approaches and analyses are readily apparent to the ordinarily skilled artisan given the guidance herein.

Compositions and Kits

Compositions for use in the methods of the invention, as well as kits for practice of the methods of the invention are also encompassed.

In one embodiment, the invention provides a kit suitable for the isolation of viable diseased cells and practice of the methods of preparing primary cells. This kit can be provided with instruction for the environmental conditions described herein and for the instruction for making any form of the present compositions, including culture media and attachment surfaces comprising ECM components. For example, the kit can provide separated stock components that can be combined and diluted in suitable aqueous solutions. In certain embodiments, at least some of the components of the kit are stored at different temperatures or as liquids or as powders. In certain embodiments, the kit includes coated surfaces for culturing the diseased cells on an anoikis-reducing surface, such as the surfaces described herein comprising ECM components.

In another aspect, the invention provides a cell culture composition comprising primary human cancer cells cultured in a media comprising at least one anoikis inhibitor under conditions comprising greater than 2% and less than 20% oxygen. In one embodiment of the cell culture composition, the media comprises at least one inhibitor of an intrinsic anoikis pathway and at least one inhibitor of an extrinsic anoikis pathway and wherein the cells are cultured under conditions comprising 6-17% oxygen (e.g., 10% oxygen). In another embodiment of the cell culture composition, the media comprises at least one inhibitor of an intrinsic anoikis pathway, at least one inhibitor of an extrinsic anoikis pathway and wherein the cells are cultured under conditions comprising 6-17% oxygen (e.g., 10% oxygen). In yet other embodiments, the media comprises one or more additional components as described in the section above on use of multiple culture media in combination.

In another aspect, the invention provides a biosensor surface comprising primary human cancer cells attached to the biosensor surface via a hydrated extracellular matrix (ECM), wherein the ECM consists of: (i) fibronectin and collagen; (ii) collagen and laminin 332 (laminin V) or (iii) laminin 332 (laminin V). In one embodiment, the ECM consists of fibronectin and collagen, preferably comprising a fibrillic and hydrophilic surface. In another embodiment, the ECM consists of collagen and laminin 332 (laminin V). In yet another embodiment, the ECM consists of laminin 332 (laminin V). In one embodiment, the hydrated ECM is folded.

In another aspect, the invention provides a cell culture vessel surface comprising primary human cancer cells attached to the cell culture vessel surface via a hydrated extracellular matrix (ECM), wherein the ECM consists of: (i) fibronectin and collagen; (ii) collagen and laminin 332 (laminin V) or (iii) laminin 332 (laminin V). In one embodiment, the ECM consists of fibronectin and collagen, preferably comprising a fibrillic and hydrophilic surface. In another embodiment, the ECM consists of collagen and laminin 332 (laminin V). In yet another embodiment, the ECM consists of laminin 332 (laminin V). In one embodiment, the hydrated ECM is folded.

Clinical Testing

The method of the invention for preparing primary cells for clinical testing can optionally include, after the culture step(s), a step of conducting a clinical test of the sample of cells. Thus, at the proper time before testing, the viable diseased patient cell sample can be removed from the above-described anti-anoikis preparation conditions in order to conduct one or more clinical tests on the sample. The clinical test(s) can be any clinical test that uses primary cells designed to provide clinically relevant and/or useful results, including but not limited to diagnostic tests, genetic tests, and tests to determine the efficacy of particular treatment regimens.

In one embodiment, the clinical test is conducted using a biosensor. Accordingly, the methods of the invention, the sample of viable disease cells can be attached to a biosensor surface prior to clinical testing (e.g., using the anti-anoikis attachment conditions described herein). Non-limiting examples of biosensor-based assays that can be carried using the cultured primary cells provided by the invention include assays for determining whether an agent(s) causes a change in the cell adhesion and signaling pathway activity of the viable disease cells, such as the assays described in U.S. Patent Publications 20130330761 and 20150125894 by Laing et al., the entire contents of both of which are specifically incorporated herein by reference in their entirety.

In one embodiment, a sample of viable diseased cells prepared according to any of the culturing methods described herein is evaluated to determine whether the addition of agents causes a change in the cell adhesion and signaling pathway activity of the viable disease cells. In certain embodiments, these cell preparation methods are combined with a method of evaluating whether a first agent that is a targeted therapeutic has an effect on a signaling pathway it is intended to address in order to determine whether the targeted therapeutic is functional in the subject's cancer cells. Such a method can comprise:

culturing the sample of viable cancer cells obtained from the subject in a media free of serum, wherein the media can further contain any of the anti-anoikis components or conditions described herein;

contacting the sample with a first agent and with a second agent that is known to selectively affect the same signaling pathway the first agent is intended to address, so as to upregulate or down-regulate the signaling pathway as measured by an effect on cell adhesion or attachment, to produce a sample contacted with both the first agent and the second agent;

continuously measuring cell adhesion or attachment of viable cells in the sample contacted with both the first agent and the second agent, relative to a sample of viable cancer cells obtained from the subject which sample is contacted with the first agent or the second agent alone;

determining by mathematical analysis of the continuous measurements whether a change in cell adhesion or attachment has occurred in the sample contacted with both the first agent and the second agent, as compared to the sample contacted with the first agent or the second agent alone; and selecting the first agent for therapeutic use in the subject wherein the first agent, in combination with the second agent, causes a change in cell adhesion or attachment, as compared to the first or second agent alone, indicating the first agent is functional in the cell signaling pathway of the subject's cancer cells.

In other embodiments, these cell preparation methods are combined with a method of evaluating whether a therapeutic that targets a HER family receptor is functional in a sample of viable cancer cells obtained from a subject. Such an evaluation method can comprise:

culturing the sample of viable cancer cells obtained from the subject in a media free of serum and growth factors;

contacting (1) a first portion of the sample with a therapeutic targeting a HER family receptor and with neuregulin, and/or (2) contacting a second portion of the sample with a therapeutic targeting a HER family receptor and with an epidermal growth factor;

continuously measuring cell adhesion or attachment of viable cells (1) in the first portion of the sample contacted with both the therapeutic and neuregulin, relative to a sample of viable cancer cells obtained from the subject which sample is contacted with the therapeutic or neuregulin alone, and/or (2) in the second portion of the sample contacted with both the therapeutic and an epidermal growth factor, relative to a sample of viable cancer cells obtained from the subject which sample is contacted with the therapeutic or an epidermal growth factor alone;

determining by mathematical analysis of the continuous measurements whether a change in cell adhesion or attachment has occurred (1) in the first portion contacted with both the therapeutic and neuregulin, as compared to the sample contacted with the therapeutic or neuregulin alone, and/or (2) in the second portion contacted with both the therapeutic and an epidermal growth factor, as compared to the sample contacted with the therapeutic or an epidermal growth factor alone; and selecting the therapeutic to treat the subject wherein a change in cell adhesion or attachment occurs (1) in the first portion, as compared to the therapeutic or neuregulin alone, and/or (2) in the second portion, as compared to the therapeutic or an epidermal growth factor alone, indicating the therapeutic is functional in the subject's cancer cells.

In embodiments, a sample of viable diseased cells prepared according to any of the culturing methods described herein are evaluated to determine whether the addition of an agent(s) causes a change in the cell adhesion and signaling pathway activity of the viable disease cell. In certain embodiments, these cell preparation methods are combined with a method of evaluating whether a first agent that is a targeted therapeutic has an effect on a signaling pathway it is intended to address in order to determine whether the targeted therapeutic is functional in the subject's cancer cells. Such a method can comprise:

culturing the sample of viable cancer cells obtained from the subject in a media free of serum and containing selected natural agents or factors known to affect cell signaling function that may lead to sensitivity or resistance to the targeted therapeutic or the second agent;

contacting the sample with a first agent and with a second agent that is known to selectively affect the same signaling pathway the first agent is intended to address, so as to upregulate or down-regulate the signaling pathway as measured by an effect on cell adhesion or attachment, to produce a sample contacted with both the first agent and the second agent;

continuously measuring cell adhesion or attachment of viable cells in the sample contacted with both the first agent and the second agent, relative to a sample of viable cancer cells obtained from the subject which sample is contacted with the first agent or the second agent alone;

determining by mathematical analysis of the continuous measurements whether a change in cell adhesion or attachment has occurred in the sample contacted with both the first agent and the second agent, as compared to the sample contacted with the first agent or the second agent alone; and selecting the first agent for therapeutic use in the subject wherein the first agent, in combination with the second agent, causes a change in cell adhesion or attachment, as compared to the first or second agent alone, indicating the first agent is functional in the cell signaling pathway of the subject's cancer cells in the presence of the resistance or sensitivity agent or factor.

Clinical testing carried out using primary cells prepared according to the methods described herein, and/or using the compositions described herein (e.g., primary cell cultures, cell culture vessel surfaces, biosensor surfaces) can be used for diagnostic purposes, e.g., to diagnose whether a subject from whom the primary cell sample is obtained has a particular disease or disorder (e.g., cancer, an autoimmune disease etc.), wherein the diagnostic criteria based on the outcome of the clinical testing has been determined.

Furthermore, the subject from whom the primary cell sample is obtained can be treated based on the outcome of the clinical testing (e.g., a treatment regimen can be selected based on the outcome of the clinical testing). For example, in one embodiment, the cell preparation methods and compositions described herein are combined with a method of treating a human subject diagnosed with cancer, wherein the selected treatment regimen is based on the outcome of clinical testing using the cell preparation methods and compositions described herein. In one embodiment, this method of treating a human subject diagnosed with cancer comprises:

administering to the subject a first agent that is a targeted therapeutic that has been determined to be therapeutically active in the signaling pathway it is intended to address in the subject's cancer cells, by a method comprising:

culturing a sample comprising of viable cancer cells (e.g., primary and/or metastatic cancer cells) obtained from the subject (e.g., according to the culturing methods described herein);

contacting the sample with the first agent and with a second agent that is known to selectively affect the same signaling pathway the first agent is intended to address, so as to upregulate or downregulate the signaling pathway as measured by an effect on cell adhesion or attachment, to produce a sample contacted with both the first agent and the second agent;

continuously measuring cell adhesion or attachment of viable primary or metastatic cancer cells in the sample contacted with both the first agent and the second agent, relative to a sample of viable cancer cells obtained from the subject which sample is contacted with the first agent or the second agent alone (e.g., using a biosensor, wherein the viable cells are attached to the biosensor surface according to the methods described herein);

determining by mathematical analysis of the continuous measurements an output value, expressed as a percentage, that characterizes whether a change in cell adhesion or attachment has occurred in the sample contacted with both the first agent and the second agent, as compared to the sample contacted with the first agent or the second agent alone; and administering the first agent to the subject wherein the output value that characterizes the change in cell adhesion or attachment is equal to or greater than a threshold value (e.g., 50%), indicating the first agent is therapeutically active in the cell signaling pathway of the subject's cancer cells.

Definitions

Unless defined otherwise, all technical and scientific terms used herein have the same meaning as is commonly understood by one of ordinary skill in the art to which this invention belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference. The following terms, as used herein, are intended to have the following definitions.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5).

The term "activator," "activate," or "perturbant," "perturb," "perturbation" in conjunction with respect to cells refer to the specific subject or activity of physiologic manipulation of a cell using reagents, organic molecules, signaling factors, biochemicals, nucleic acids, or proteins that have an effect on cells well known to those practiced in the art. The effect refers to any modulation of cellular physiologic activity and may include but not be limited to up or down-regulation.

The term "anoikis" refers to an activity leading to quiescence, senescence, and eventually can lead to cell death that is induced by signaling of adhesion molecules of anchorage-dependent cells as they are detaching from the surrounding extracellular matrix (ECM) and neighboring cells. Usually cells stay close to the tissue to which they belong since the communication between proximal cells as well as between cells and ECM provide essential signals for regulating growth and survival. When cells are detached from their native ECM or their neighbors, there is a loss of normal cell—matrix and cell-cell interactions, and the cells will initiate anoikis signaling. The present invention is aimed at preventing anoikis signaling of primary cells and anoikis-related activities of primary patient diseased cells such that said cells may be used in a clinical test of the patient's functional cells that may rely upon measuring response to perturbants via adhesion-related mediated signaling.

The term "antibiotic" refers to chemical substances natural or synthetic of relatively low molecular weight that inhibit growth of non-mammalian cells. First discovered naturally where they were produced by various species of microorganisms, such as bacteria, actinomycetes, and fungi, they may be synthesized chemically, or natural compounds may be chemically modified to produce semisynthetic antibiotics. The major classes of antibiotics are: (1) beta-lactams, including the penicillins, cephalosporins and monobactams; (2) aminoglycosides, e.g., gentamicin, tobramycin, netilmycin, and amikacin; (3) tetracyclines; (4) sulfonamides and trimethoprim; (5) fluoroquinolones, e.g., ciprofloxacin, norfloxacin, and ofloxacin; (6) vancomycin; (7) macrolides, which include for example, erythromycin, azithromycin, and clarithromycin; and (8) other antibiotics, e.g., the polymyxins, chloramphenicol and the lincosamides. Commercially available mixtures are included (e.g. P/S/A-penicillin-streptomycin-amphotericin B, also known as antibiotic-antimycotic solution).

The term "apoptosis" refers to programmed cell death and is a key regulatory system of physiological growth control and regulation of tissue homeostasis. Apoptosis plays a critical role in the regulation of tumor formation. Many anticancer therapies are designed to activate apoptosis signal transduction pathways in cancer cells Apoptosis can be a stage after anoikis in some cells.

The term "anoikis inhibitor" refers to molecules or conditions that either inhibit pro-anoikis function or allow anti-anoikis activation of intrinsic or extrinsic signal transduction pathways and thereby suppress anoikis. Preferred inhibitors in the present invention are reversible after a period of time. A reversible inhibitor in this case involves inhibition caused by application of a reagent whose effect on anoikis is not sustained upon removal of the reagent. Reversible inhibitors are desirable so that patient samples are returned to their in-vivo-like state before testing.

The term "assay" or "assaying" refers to an analysis to determine, for example, the presence, absence, quantity, extent, kinetics, dynamics, or type of a target, such as a cell's optical or bioimpedance response upon stimulation with exogenous stimuli (e.g., therapeutic agent).

The terms "attach," or "attachment," refer to, for example, a surface modifier substance, a cell, a ligand candidate compound, and like entities of the disclosure, connected to a surface, such as by physical absorption, chemical bonding, chemical attraction, and like processes, or combinations thereof. Particularly, "cell attachment," "cell adhesion," or "cell sample attachment" refer to the binding of cells together or interacting to a surface, such as by culturing, or interacting with a cell anchoring material, or the like.

The term "attachment pattern" refers to observable traits or characteristics of a cell or cell sample's connection to a surface. An attachment pattern can be quantitative, e.g., number of attachment sites. An attachment pattern can also be qualitative, e.g., preferred molecular site of attachment to a hydrated extracellular matrix.

The term "basal morphology" refers to the form and structure of a cell or cell sample prior to the introduction of an agent or stimulus.

The term "baseline measurement" refers to a physiologic beginning point for a set of cells to be tested and is based on an evaluation of measurements over a period of time before drug is added.

The term "biosensor" refers to a device that measures an analyte or a change in an analyte or physiologic condition of a cell. In embodiments, the biosensor typically contains three parts: a biological component or element that binds or recognizes the analyte (including non-limiting examples such as extracellular matrix, cell signaling molecule, or cell proliferation, tissue, cells, metabolites, catabolites, biomolecules, ions, oxygen, carbon dioxide, carbohydrates, proteins etc.), a detector element (operating in a physicochemical manner such as optical, piezoelectric, electrochemical, thermometric, or magnetic), and a transducer associated with both components. The term "biosensor" encompasses optical biosensors and impedance biosensors. The term "optical biosensor" refers to a device that measures fluorescence, absorption, transmittance, density, refractive index, and reflection of light. In embodiments, an optical biosensor can comprise an optical transducer for converting a molecular recognition or molecular stimulation event in a living cell, a pathogen, or combinations thereof into a quantifiable signal. Additionally, embodiments could include a photonic crystal device, an optical waveguide device, and a surface plasmon resonance device. The term "impedance biosensor" refers to a device that measures complex impedance changes (delta Z, or dZ) of live patient cells where impedance (Z) is related to the ratio of voltage to current as described by Ohm's law ($Z=V/I$). It is sensitive to the local ionic environment at the electrode interface with the cells and detects these changes as a function of voltage and current fluctuations. Physiologic changes of the cells as a result of normal function or perturbation thereof result in quantifiable changes to the flow of current around the electrodes and influence the magnitude and characteristics of the signal measured. In embodiments, an impedance biosensor can comprise electrodes or an electrical circuit for converting a molecular recognition or molecular stimulation event in a living cell, a pathogen, or combinations thereof into a quantifiable signal. In embodiments, an ISFET biosensor can comprise an ion selective field effect electrical transducer for converting an analyte recognition or cellular stimulation event in a living cell, a pathogen, or combinations thereof into a quantifiable signal. When an analyte concentration in an ISFET biosensor changes, the current in the transistor changes, which creates a quantification signal.

The term "cell adhesion" refers to the binding of a cell to another cell, to an extracellular matrix component, or to a surface (e.g., microtiter plate).

The term "cell proliferation" refers to an increase in the number of cells as a result of cell growth and cell division.

The term "cell sample" refers to cells isolated from a particular subject, where the cells are isolated from a subject's biological fluids, excretions, or tissues. Cells isolated from tissue can include tumor cells. Cells isolated from tissue include homogenized tissue, and cellular extracts, and combinations thereof. Cell samples include isolation from, but are not limited to, breast tissue, stomach tissue, colon/intestinal tissue, lung tissue, head tissue, neck tissue, parotid tissue, ovarian tissue, uterine tissue, cervical tissue, prostate tissue, pancreatic tissue, kidney/renal tissue, or bone and/or bone marrow, blood, blood serum, blood plasma, urine, semen, seminal fluid, seminal plasma, prostatic fluid, pre-ejaculatory fluid (Cowper's fluid), excreta, tears, saliva, sweat, biopsy of any practical form, ascites, surgical resection, cerebrospinal fluid, lymph, marrow, or hair.

The term "cell signaling" refers to the intracellular or intercellular transfer of information. Cells signaling can be achieved by direct contact between cells, between cells and ECM, or by the release of a substance from one cell that is taken up by another cell. Intercellular signaling can occur via an interaction between two molecules (e.g., a ligand and a receptor). Receptor binding can trigger a cascade of intracellular signaling (e.g., initiation of biochemical changes within the cell or modification of the membrane potential).

The term "cell survival" refers to the viability of a cell characterized by the capacity to perform certain functions such as metabolism, growth, movement, reproduction, some form of responsiveness, and adaptability.

The term "chemically defined" means the structures, chemical formula, and the composition and percentage of the various individual components within a chemical composition are known or can be defined. To this end, in the present invention the medium does not contain any animal serum typically prepared for tissue culture purposes. Nor does it contain any tissue extracts with unknown/undefined chemical components. All essential components necessary to support the desired growth/proliferation of a heterogenous population of diseased cell types from individual patients are chemically defined.

The term "cytoskeletal organization" refers to the arrangement of the internal scaffold of a cell. A cell's cytoskeleton comprises filaments that serve to support cytoplasmic or membrane elements and/or intracellular organelles. The cytoskeleton also helps to maintain the shape of a cell.

The terms "diseased cell sample" or "diseased cell population" or "diseased cell" refer to a mixture of diseased cells, especially epithelial cells that are extracted from an individual patient's tumor or tumors or diseased tissue or fluid. The disease cell sample may be from tissue or fluid that is characterized by abnormal growth. The sample of cells is heterogeneous in the composition of particular sub-types and can be comprised of, for example, luminal, myo-, basal, stem, cells on the epithelial mesenchymal continuum, differentiated or undifferentiated, or especially mixtures of all the above where they represent the in vivo condition of a patient's tumor. It is recognized that particular cancer intrinsic subtypes may have differential percentages of certain types of diseased cells (e.g. ER+ breast cancer is known as a luminal epithelial cancer and thus may have a high proportion of extracted cells of luminal lineage and a lesser percentage of other epithelial types. Another example—triple negative breast cancer is known as a basal epithelial cancer and thus may have a high proportion of extracted diseased cells of basal lineage and a lesser percentage of other epithelial types). The sample may be comprised especially of viable, or replication competent, or dividing, or non-dividing, or at any point or combinations of points in the cell cycle. Cells may be entering or not entering anoikis, or fully engaged at any level in anoikis. Samples of cells may be selected on the basis of their disease pathway activity.

The terms "extracellular matrix component" or "ECM component" refer to a molecule that occurs in the extracellular matrix of an animal. The molecule can be a component of an extracellular matrix from any species and from any tissue type. Non-limiting examples of extracellular matrix components include laminins, collagens, fibronectins, other glycoproteins, peptides, glycosaminoglycans, proteoglycans, etc. Extracellular matrix components can also include growth factors.

The term "extracellular matrix coating" refers to a coating on a cell culture surface that comprises one or more molecules that are naturally occurring biomolecules or biochemicals, or biochemicals derived from or based on one or more naturally occurring biomolecules or biochemicals, that may be found in an extracellular matrix. For example, an extracellular matrix coating can comprise e.g., fibronectin, collagens, laminins, other glycoproteins, peptides, glycosaminoglycans, proteoglycans, vitronectin, Intercellular-CAMs, VascularCAMs, MAdCAMs), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals. Coatings can also include cell surface receptor or cell surface cognate binding proteins or proteins with affinity for said cell surface proteins. Ideally an extracellular matrix used for coating is selected from the available genus and species by matching the ECM molecule to a specific cell type and signaling pathway.

The term "extrinsic anoikis" refers to activity associated with the extrinsic signal transduction pathways of a viable cell. Extrinsic pathways can be activated by death receptors on the plasma membrane such as for example tumor necrosis factor receptor 1 (TNFR1) and Fas/CD95. As ligands bind to these receptors, the death inducing signaling complex (DISC) is formed leading to initiation of enzyme cascades of which the caspase cascade is a member and further downstream anoikis events.

The term "extrinsic anoikis inhibitor" refers to an agent that inhibits anoikis by affecting (e.g., interfering with) the extrinsic anoikis pathway, for example an agent that inhibits the activity of a death receptor (e.g., TNFR1, ALK5/TGFBR1, Fas/CD95) on the plasma membrane. Non-limiting examples of extrinsic anoikis inhibitors include agents that bind to or otherwise inhibit the activity of the death receptor, such as antibodies and Ig fusion proteins (e.g., directed against TNFR1, ALK5/TGFBR1 or Fas/CD95), as well as agents that bind to or otherwise inhibit the activity of a ligand for the death receptor, such as antibodies and Ig fusion proteins (e.g., directed against TFNα, TGFβ or FasL). Other non-limiting examples of extrinsic anoikis inhibitors include small molecule agents that inhibit signaling through a death receptor (e.g., inhibit signaling through TNFR1, ALK5/TGFBR1 or Fas/CD95), WNT signaling agonists. Other non-limiting examples of extrinsic anoikis inhibitors include integrin stabilizers and integrin ligands that inhibit anoikis.

The term "folded extracellular matrix" refers to an ECM that is a reproducible, ordered, and structured arrangement of protein component(s) in their natural or native states comprising the ECM.

The term "healthy cell sample" refers to a cell sample wherein the cells do not have or are extracted from a tissue that does not have the disease that is being tested. For example, when a particular subject is being tested for the effects of a therapeutic agent against the subject's breast cancer, non-cancerous cells or cells from non-breast tissue are considered "healthy". The term "healthy cell sample" is not a determination or reflection upon the whole health status of the subject.

The term "hydrated extracellular matrix" refers to extracellular matrix prepared from extracellular matrix components that has been applied to a surface intended for human cells to attach and which, after application to a surface, retains sufficient water such that the ECM is fully wetted and is never allowed to dehydrate prior to use.

The term "hypoxia" refers to cell sample conditions that are less than 20.094% partial pressure of oxygen (so called normoxic). The partial pressure of oxygen in the atmosphere is 20.094% at sea level and most cancer cells are reported to experience less than 2% partial pressure of oxygen in vivo. Very low oxygen levels and high oxygen levels such as normoxia, 20% oxygen, are reportedly cause for most cells and especially primary cells to enter anoikis.

The term "intrinsic anoikis" refers to activity associated with the intrinsic signal transduction pathways of a viable cell. Intrinsic anoikis pathways are characterized by permeabilization of the mitochondrial membrane and release of cytochrome c into the cytoplasm. Cytochrome c can then form a multi-protein complex and initiates activation of the caspase cascade and further downstream anoikis events.

The term "intrinsic anoikis inhibitor" refers to an agent that inhibits anoikis by affecting (e.g., interfering with) the intrinsic pathway, for example an agent that inhibits the permeabilization of the mitochondrial membrane and/or release of cytochrome C into the cytoplasm. Non-limiting examples of intrinsic anoikis inhibitors include stress inhibitors, such as redox buffering agents and reactive oxygen species inhibitors.

The term "sample" refers to anything which may contain a moiety to be isolated, manipulated, measured, quantified, detected or analyzed using apparatuses, microplates or methods in the present disclosure. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

The terms "serum-free" or "media free of serum" refer to cell culture medium that contains essentially no serum or tissue extracts. In certain embodiments, there is 0% (completely free), or less than about 0.001%, 0.005%, 0.01%, 0.10%, or 1.0% total serum in the medium. Examples of types of serums include: various forms of bovine serum (calf serum, fetal bovine serum, bovine calf serum, donor bovine calf serum, defined fetal bovine serum, newborn bovine calf serum, etc.), horse serum and human serum, dextran extracted serums, heat inactivated serums, gamma-irradiated serums, heat-inactivated-dextran-extracted serums.

The term "shared pathway anoikis inhibitor" refers to an agent that inhibits anoikis by affecting (e.g., interfering with) a cellular signaling pathway or component that is shared by the intrinsic and extrinsic anoikis pathways such that the shared inhibitor may be effective in inhibiting both extrinsic anoikis and intrinsic anoikis. Non-limiting examples of shared pathway anoikis inhibitors include Rho-associated kinase inhibitors, caspase inhibitors, matrix metalloprotease inhibitors, WNT signaling agonists, and cytochrome C inhibitors.

The term "substantially free" refers to at least about 90%, preferably 95%, 99% or greater percentage isolated from other components. The components for example may be other cells, reagents, proteins, peptides, compounds or compositions described herein.

The term "synergy" or "synergistic effect" refers to an interaction of two or more agents wherein the combined effect of the two or more agents is greater than the sum of the separate (individual) effects of each agent.

The terms "targeted pathway drug," "pathway drug," or "targeted drug," refer to any molecule or antibody with therapeutic capacity designed to bind to a specific biomolecule (e.g. protein) involved in a disease process, thereby regulating its activity.

The term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term encompasses those compounds or chemicals traditionally regarded as drugs, vaccines, and biopharmaceuticals including molecules such as proteins, peptides, hormones, nucleic acids, gene constructs and the like. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Therapeutic agents include, but are not limited to, anticancer therapeutics, antipsychotics, anti-inflammatory agents, and antibiotics.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, patents, patent publications, references, publications, databases, database entries, and art cited herein, are incorporated into this application by reference in their entirety, even if not expressly stated in the citation. In case of conflicting statements of a cited source and the instant application, the statement in the instant application shall control.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Discussion of Experimental Design

The methods for obtaining and culturing primary diseased cells as described in the present invention are used to prepare diseased cells for a clinical test.

It is commonly understood that biochemical principles of protein binding and anoikis are universal across different cell types that attach to ECM, independent of their tissue of origin. The methods described herein are thus broadly applicable to all cell types that are attachable to an ECM regardless of their tissue of origin.

The three examples provided below demonstrate various embodiments of the methods for preparing primary cells for clinical testing described herein. In particular, the examples demonstrate the advantages that occur when: 1) 10% oxygen conditions, or 2) one or more anoikis inhibitors, or 3) hydrated and folded ECM are used when culturing a cell sample. Each of these three variables are evaluated in isolation relative to conventional conditions using a "one variable at a time" methodology. When these variables are isolated in the three examples, they are labeled for discussion purposes as the "improved" conditions and the conditions they are compared to are labeled as the "conventional" condition.

Example 1—Comparison of culturing methods under different oxygen conditions

Example 2—Comparison of culturing methods with and without one or more anoikis inhibition molecules Example 3—Comparison of culture methods with and without hydrated folded ECM Elements Used in Examples Tissue: Diseased breast tissue obtained from two different patient specimens was used in these examples (C54, C517A). Hypertrophic and breast cancer tissue provides exemplary tissue models since their mechanisms of anoikis and anoikis regulation are representative of other diseased tissue types. In addition, breast cancer accounts for over 20% of all cancers diagnosed annually in the United States, and it is the most common form of cancer in women. Tissue from the patients were obtained using tissue specimen collection techniques as described herein. Each cell sample tested was extracted from separate aliquots of diseased breast tissue. Each specimen aliquot consisted of 30 milligrams of tissue.

Cells: Diseased epithelial cells extracted from patient breast tissue specimens were selected for testing. Epithelial cells are an exemplary cell model since the mechanisms of anoikis and anoikis regulation found in them are representative of other tumor cell types.

Anoikis inhibitors. Three anoikis inhibitor molecules were used in these experiments—Rho-Kinase inhibitor, Caspase Inhibitor, and MMP3 Inhibitor—alone and in combination. Each of these affect different anoikis regulatory pathways and their associated function, including how they are extensively interconnected, regulated through binding, involve enzymatic activities such as protein cleavage, phosphorylation and de-phosphorylation, and control critical cellular functions.

Extracellular matrix (ECM) coating. Two types of ECM coating were evaluated: 1) hydrated and folded; 2) non-hydrated and non-folded. Each coating was comprised of human collagen I and human fibronectin.

Oxygen. Atmospheric conditions with three different oxygen concentrations were evaluated: 1) 2% oxygen; 2) 10% oxygen; 3) 20% oxygen.

Assessment of Culture Conditions

Two key goals when culturing a diseased cell sample are to expand the size of the cell colonies and the number of cells available for testing. A set of culture conditions that results in both higher cell count and cell colony size compared to the results from a different set of conditions is superior.

In each of the three following examples, cell samples were cultured under identical conditions, except for one variable, and then compared. To compare the effect a specific culture condition variable has on a cell sample obtained from the same patient, two different metrics were used—cell count and cell colony size change. Cell count allows for a side by side comparison of the increase in number of cells produced under different culture conditions. Cell colony size allows for a comparison of the change in the size of cell colonies produced under different culture conditions. Each metric provides a different insight into the status of a cell sample after being cultured. Cell count provides a short-term assessment of the culture conditions whereas cell colony size change gives an indication about the overall longer-term robustness of the cell sample.

Each of the three different examples are designed to isolate the effect one of three key variables—atmospheric oxygen concentration, presence or absence of anoikis inhibitors, and the type of ECM coating—has on a cell sample. In each example, an "improved" condition is tested relative to a "conventional" condition. The improved condition is intended to improve the results of the cell culture by reducing the deleterious effects of anoikis on the cell sample. In each example, cell count and cell colony size is measured after the cell sample has been cultured for a number of days to measure the effect of ameliorating anoikis within a cell sample. If one set of conditions results in both higher cell count and cell colony size, then those conditions would be deemed superior relative to its comparator.

Cell Count. An electronic cell counting instrument, Countess (Life Technologies), was used to count the number of cells in a cell sample at the end of each experiment. In each example, two cell samples derived from two separate tissue aliquots from the same patient are tested side-by-side under two different conditions. Prior to counting, the cell sample was treated with trypan blue to enable distinction between live and dead cells. Only live cells (those not stained by the trypan blue) were counted. All cell samples were counted in duplicate after five days in culture and the cell counts and are reported. The cell counts from each cell sample cultured side-by-side are compared by calculating the relative percentage difference between the "improved" cell culture and the "conventional" cell culture. A cell culture condition that yielded a higher cell number count after five days relative to its comparator was deemed superior.

Cell colony size. To quantify the change in the size of cell colonies in a cell sample, an assessment of the size of four cell colonies is made at a first (early) date after initiation of culturing and compared to the sizes of those four colonies at a second, later date. The first image is taken 48 hours after culture initiation and the second image is taken 48-96 hours later. To measure colony size, images of colonies are made using a 40× inverted microscope and the area of the cell colonies is then quantified by determining the number of pixels each colony covers. The absolute change in the total size of the four colonies between the first and second images is calculated for each cell sample under the two different conditions and reported. This change in colony size is then compared by calculating the relative percentage difference between the "improved" cell culture and the "conventional" cell culture. A cell culture condition that yielded a larger change in cell colony size relative to its comparator was deemed superior.

Example 1: Comparison of Culturing Methods Under Three Different Oxygen Conditions In this example, primary cell samples from patient C517 were prepared in an extraction culture media and an initial culture media that contained at least one anoikis inhibitor on a cell culture surface comprised of a hydrated and folded ECM coating under three different oxygen conditions: 1) 10% oxygen conditions (the "improved" condition); 2) hypoxic (2%) oxygen conditions; 3) normoxic (20%) conditions. The 2% and 20% oxygen conditions represent the "conventional" condition.

The cell sample for this example was prepared as follows:

A human diseased tissue specimen was obtained and initially prepared by removing obviously fatty portions and mincing the specimen into 1-4 mm size pieces. The minced specimen was then separated into aliquots, each 30 milligrams in size.

Diseased cells were extracted from the minced specimen sample aliquot by tumbling the sample in an extraction media for at least three hours ("extraction period") that was serum free and included DMEM/F12 media, a mixture of collagenases and hyaluronidase (digestion enzymes), and at least one anoikis inhibitor molecule. In addition, the media comprised additional components, including: epidermal growth factors, estradiol, Ca2+, Mg2+, tri-iodothyronine, tetra-iodothyronine, glutathione, adenine.

The cells extracted from the tissue sample were recovered from the extraction media and plated on a surface comprising a hydrated and folded extracellular matrix consisting of a combination of collagen and fibronectin.

The cell sample was then cultured in the media used for extraction (described above) but with the digestion enzymes (collagenases and hyaluronidase) removed.

All tissue samples were cultured at 37° C., 5% $CO_2$, 85% relative humidity and either 2%, 10%, or 20% oxygen (the variable condition being evaluated).

The cells were then removed from the culture vessel by treatment with a gentle enzyme removal process, followed by washing and transfer to a test vessel.

Results for the three samples cultured are shown in Tables 3 and 4. In each table, the "improved" condition (10% oxygen) is compared to the conventional condition (2% or 20% oxygen). Cell count and cell colony size change and the percent difference between the optimized condition and the conventional condition is reported. Cell colony size change is reported in pixels.

TABLE 3

10% vs. 2% Oxygen

| Metric | 10% O$_2$ (Improved) | 2% O$_2$ (Conventional) | Difference (Improved vs. Conventional) |
| --- | --- | --- | --- |
| Cell count (live only) | 141,225 | 6,818 | 1971% |
| Cell colony size change (pixels) | 552,025 | 62,442 | 784% |

Both cell count and cell colony size were dramatically higher under the 10% oxygen conditions compared to the 2% conditions. These demonstrate the superiority of using 10% oxygen versus 2% oxygen (hypoxia) conditions when culturing live cell samples.

TABLE 4

10% vs. 20% Oxygen

| Metric | 10% O$_2$ (Improved) | 20% O$_2$ (Conventional) | Difference (Improved vs. Conventional) |
| --- | --- | --- | --- |
| Cell count (live only) | 141,225 | 19,988 | 606% |
| Cell colony size change (pixels) | 552,025 | 75,087 | 635% |

Both cell count and cell colony size were dramatically higher under the 10% oxygen conditions compared to the 20% conditions. These results thus demonstrate the superiority of using 10% oxygen versus 20% oxygen (normoxic) conditions when culturing live cell samples.

In summary, these examples demonstrate the superiority of culturing cells in atmospheric conditions that are below normoxic conditions (20%) and above hypoxic conditions (2%). The results for 2% and 20% conditions were comparable, which suggests that cell sample results improve as the oxygen concentration converges on 10%. Thus, the ordinarily skilled artisan will readily appreciate the results presented herein that any oxygen concentration higher than 2% and lower than 20% is superior to the hypoxic (2%) or normoxic (20%) oxygen concentrations typically used to culture cells.

Example 2: Comparison of Culturing Methods with and without One or More Anoikis Inhibition Molecules In this example, primary cell samples from two patients, C54 and C517, were tested to isolate the effect anoikis inhibitor molecules have on cell count and cell colony size. Each cell sample was cultured on a cell culture surface comprised of a hydrated and folded ECM coating and under 10% oxygen conditions. The samples were cultured in one of five different culture medias differentiated only by the absence of any anoikis inhibitor molecules or the presence of one of three different anoikis inhibitor molecules alone or in combination, as follows: 1) no anoikis inhibitor molecules; 2) a caspase inhibitor; 3) an MMP3 inhibitor; 4) a Rho-associated kinase inhibitor; 5) a combination of caspase, MMP3 and Rho-associated kinase inhibitors.

The cell sample for this example was prepared as follows:

A human diseased tissue specimen was obtained and initially prepared by removing obviously fatty portions and mincing the specimen into 1-4 mm size pieces. The minced specimen was then separated into aliquots, each 30 milligrams in size.

Diseased cells were extracted from the minced specimen sample aliquot by tumbling the sample in an extraction media for at least three hours ("extraction period") that was serum free and included DMEM/F12 media, a mixture of collagenases and hyaluronidase (digestion enzymes), and either: 1) no anoikis inhibitors; 2) a caspase inhibitor; 3) an MMP3 inhibitor; 4) a Rho-associated kinase inhibitor; or 5) a combination of caspase, MMP3 and Rho-associated kinase inhibitors (the variable condition being evaluated). In addition, the media in each of the five different alternative medias evaluated comprised additional components, including: epidermal growth factors, estradiol, Ca2+, Mg2+, tri-iodothyronine, tetra-iodothyronine, glutathione, adenine.

The cells extracted from the tissue sample were recovered from the extraction media and plated on a surface comprising a hydrated and folded extracellular matrix consisting of a combination of collagen and fibronectin.

The cell sample was then cultured in the media used for extraction (described above) but with the digestion enzymes (collagenases and hyaluronidase) removed.

All tissue samples were cultured at 37° C., 5% CO$_2$, 85% and 10% oxygen.

The cells were then removed from the culture vessel by treatment with a gentle enzyme removal process, followed by washing and transfer to a test vessel.

Results for the three samples cultured are shown in Tables 5-8. In each table, the "improved" condition (one or more anoikis inhibitor) is compared to the conventional condition (no anoikis inhibitor). Cell count and cell colony size change and the percent difference between the optimized condition and the conventional condition is reported. Cell colony size change is reported in pixels.

TABLE 5

Rho-Kinase anoikis inhibitor vs. no anoikis inhibitor molecule (Patient C517)

| Metric | RhoKinase Inhibitor (Improved) | No Inhibitor (Conventional) | Difference (Improved vs. Conventional) |
| --- | --- | --- | --- |
| Cell count (live only) | 78,750 | 51,450 | 53% |
| Cell colony size change (pixels) | 502,999 | 149,309 | 237% |

TABLE 6

Caspase anoikis inhibitor vs. no inhibitor (Patient C54)

| Metric | Caspase Inhibitor (Improved) | No Inhibitor (Conventional) | Difference (Improved vs. Conventional) |
| --- | --- | --- | --- |
| Cell count (live only) | 69,975 | 63,750 | 10% |
| Cell colony size change (pixels) | 194,095 | 118,754 | 63% |

TABLE 7

MMP3 anoikis inhibitor vs. no inhibitor (Patient C54)

| Metric | MMP3 Inhibitor (Improved) | No Inhibitor (Conventional) | Difference (Improved vs. Conventional) |
| --- | --- | --- | --- |
| Cell count (live only) | 137,700 | 63,750 | 116% |
| Cell colony size change (pixels) | 336,700 | 118,754 | 184% |

TABLE 8

Three Anoikis inhibitors vs. no inhibitor molecule (Patient C517)

| Metric | 3 Anoikis Inhibitors (Improved) | No Inhibitor (Conventional) | Difference (Improved vs. Conventional) |
|---|---|---|---|
| Cell count (live only) | 177,750 | 51,450 | 245% |
| Cell colony size change (pixels) | 552,025 | 149,309 | 270% |

Both cell count and cell colony size were higher in each cell sample that was prepared in a culture media containing one or more anoikis inhibitor molecules compared to the cell sample comparator that was cultured with no anoikis inhibitor. These results thus demonstrate the superiority of using one or more anoikis inhibitors in a culture media when culturing live cell samples. In addition, since three different anoikis inhibitor molecules affecting three different anoikis related pathways were evaluated, and each found to produce superior results, this example demonstrates that the advantages of using an anoikis inhibitor molecules are general in nature, and not restricted to one specific molecule or class of anoikis inhibitors.

Example 3: Comparison of Culture Methods with and without Hydrated Folded ECM In this example, primary cell samples from Patient C54 were tested to isolate the effect that coating a cell culture surface with hydrated and folded ECM has on cell count and cell colony size. Each cell sample was cultured under 10% oxygen conditions in a culture media containing at least one anoikis inhibitor in a cell culture vessel coated either with: 1) a hydrated and folded ECM; or 2) a non-hydrated and unfolded ECM.

The cell sample for this example was prepared as follows:

A human tumor tissue specimen was obtained and initially prepared by removing obviously fatty portions and mincing the specimen into 1-4 mm size pieces. The minced specimen was then separated into aliquots, each 30 milligrams in size.

Tumor cells were extracted from the minced specimen sample aliquot by tumbling the sample in an extraction media for at least three hours ("extraction period") that was serum free and included DMEM/F12 media, a mixture of collagenases and hyaluronidase (digestion enzymes), and at least one anoikis inhibitor molecule. In addition, the media comprised additional components, including: epidermal growth factors, estradiol, Ca2+, Mg2+, tri-iodothyronine, tetra-iodothyronine, glutathione, adenine.

The cells extracted from the tissue sample were recovered from the extraction media and plated on a surface comprising either: 1) a hydrated and folded extracellular matrix consisting of a combination of collagen and fibronectin; or 2) a non-hydrated and not folded extracellular matrix (the variable condition being evaluated).

The cell sample was then cultured in the media used for extraction (described above) but with the digestion enzymes (collagenases and hyaluronidase) removed.

All tissue samples were cultured at 37° C., 5% $CO_2$, 85% relative humidity and 10% oxygen.

The cells were then removed from the culture vessel by treatment with a gentle enzyme removal process, followed by washing and transfer to a test vessel.

Results for the two samples cultured are shown in Table 9 below. In this table, the "improved" condition (hydrated and folded ECM) is compared to the conventional condition (non-hydrated and not folded ECM). Cell count and cell colony size change and the percent difference between the optimized condition and the conventional condition is reported. Cell colony size change is reported in pixels.

TABLE 9

Hydrated/folded ECM vs non-hydrated/not folder ECM

| Metric | Hydrated & Folded (Improved) | Non-hydrated & Not folded (Conventional) | Difference (Improved vs. Conventional) |
|---|---|---|---|
| Cell count (live only) | 69,975 | 39,150 | 79% |
| Cell colony size change (pixels) | 194,095 | 50,103 | 287% |

Both cell count and cell colony size are higher in each cell sample that was prepared using hydrated and folded ECM compared to one prepared with non-hydrated and not folded ECM. These results thus demonstrate the superiority of using a cell culture vessel coated with a hydrated and folded ECM when culturing live cell samples.

The invention claimed is:

1. A method of increasing the cell count and cell colony size of viable cancer cells obtained from a human, the method comprising:
   culturing the viable cancer cells obtained from the human subject in a medium comprising at least one caspase inhibitor, at least one MMP3 inhibitor and at least one Rho-associated kinase inhibitor under conditions comprising greater than 2% and less than 20% oxygen for at least 24 hours; and
   attaching the cultured cancer cells to a surface comprising a hydrated and folded extracellular matrix (ECM).

2. The method of claim 1, wherein the viable cancer cells are cultured under conditions comprising 6-17% oxygen.

3. The method of claim 1, wherein the cultured cancer cells are transferred to a medium lacking caspase inhibitors, MMP3 inhibitors and Rho-associated kinase inhibitors under conditions comprising 20% oxygen prior to attaching the cultured cancer cells to the surface comprising a hydrated and folded ECM.

4. The method of claim 1, wherein after the cultured cancer cells are attached to the surface, a clinical test is conducted on the cultured cancer cells.

5. The method of claim 1, wherein the surface is a biosensor surface or a cell culture vessel surface.

6. The method of claim 4, wherein a clinical test is conducted on the cells attached to the surface using a biosensor.

7. The method of claim 1, which comprises:
   culturing the viable cancer cells obtained from the human subject in a medium comprising at least one digestion enzyme and at least one caspase inhibitor, at least one MMP3 inhibitor and at least one Rho-associated kinase inhibitor under conditions comprising 6-17% oxygen; followed by
   culturing the viable cancer cells in a medium comprising at least one caspase inhibitor, at least one MMP3 inhibitor and at least one Rho-associated kinase inhibitor and lacking digestion enzymes under conditions comprising 6-17% oxygen, prior to attaching the cultured cancer cells to the surface comprising a hydrated and folded ECM.

8. The method of claim 1, which comprises: culturing the viable cancer cells obtained from the human subject in a media comprising at least one caspase inhibitor, at least one MMP3 inhibitor and at least one Rho-associated kinase inhibitor under conditions comprising 6-17% oxygen on a cell culture vessel surface coated with a hydrated and folded extracellular matrix (ECM), prior to attaching the cultured cancer cells to the surface comprising a hydrated and folded ECM.

9. The method of claim 1, wherein: the cultured cancer cells are attached to a biosensor surface comprising a hydrated and folded extracellular matrix (ECM), wherein the ECM consists of: (i) fibronectin and collagen; (ii) collagen and laminin 332 (laminin V) or (iii) laminin 332 (laminin V).

10. A method of increasing cell count and cell colony size of viable cancer cells obtained from a human subject for a clinical test using a biosensor, the method comprising:
   culturing the sample of viable cancer cells obtained from the human subject in medium comprising at least one caspase inhibitor, at least one MMP3 inhibitor and at least one Rho-associated kinase inhibitor under conditions comprising 6-17% oxygen for at least 24 hours;
   attaching the cultured cancer cells to a biosensor surface comprising a hydrated and folded extracellular matrix (ECM), wherein the ECM consists of: (i) fibronectin and collagen; (ii) collagen and laminin 332 (laminin V) or (iii) laminin 332 (laminin V); and
   conducting a clinical test using a biosensor on the cultured cancer cells.

* * * * *